United States Patent
Basaric et al.

(10) Patent No.: US 11,103,519 B2
(45) Date of Patent: Aug. 31, 2021

(54) QUINONE-METHIDE PRECURSORS WITH BODIPY CHROMOPHORE, METHOD OF PREPARATION, BIOLOGICAL ACTIVITY AND APPLICATION IN FLUORESCENT LABELLING

(71) Applicant: Rudjer Boskovic Institute, Zagreb (HR)

(72) Inventors: Nikola Basaric, Zagreb (HR); Marijeta Kralj, Zagreb (HR); Ana-Matea Mikecin, Zagreb (HR); Matej Cindric, Slavonski Brod (HR)

(73) Assignee: RUDJER BOSKOVIC INSTITUTE, Zagreb (HR)

( * ) Notice: Subject to any disclaimer, the term of this patent is extended or adjusted under 35 U.S.C. 154(b) by 350 days.

(21) Appl. No.: 16/612,371

(22) PCT Filed: May 15, 2017

(86) PCT No.: PCT/HR2017/000005
§ 371 (c)(1),
(2) Date: Nov. 9, 2019

(87) PCT Pub. No.: WO2017/199056
PCT Pub. Date: Nov. 23, 2017

(65) Prior Publication Data
US 2020/0197423 A1 Jun. 25, 2020

(30) Foreign Application Priority Data
May 16, 2016 (EP) .................................... 16169771

(51) Int. Cl.
A61P 35/00 (2006.01)
C07F 5/02 (2006.01)
A61K 31/69 (2006.01)

(52) U.S. Cl.
CPC .............. *A61K 31/69* (2013.01); *A61P 35/00* (2018.01); *C07F 5/022* (2013.01)

(58) Field of Classification Search
CPC ..................................................... C07F 5/022
See application file for complete search history.

(56) References Cited

U.S. PATENT DOCUMENTS

2005/0186641 A1* 8/2005 Haugland ................ C07K 1/13
435/7.5

* cited by examiner

*Primary Examiner* — Joseph R Kosack
(74) *Attorney, Agent, or Firm* — Ted Whitlock; Registered Patent Attorney, PA

(57) ABSTRACT

The invention relates to BODIPY derivatives of Formula (I):

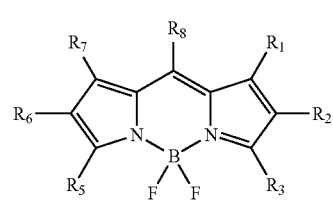

that bear one or more functional groups which in the photochemical reaction upon irradiation with visible light undergo deamination and deliver quinone methides. Furthermore, the invention relates to the antiproliferative activity of BODIPY derivatives and their use for pharmaceutical applications and for fluorescent labeling, particularly for labeling proteins.

13 Claims, 2 Drawing Sheets

Figure 2

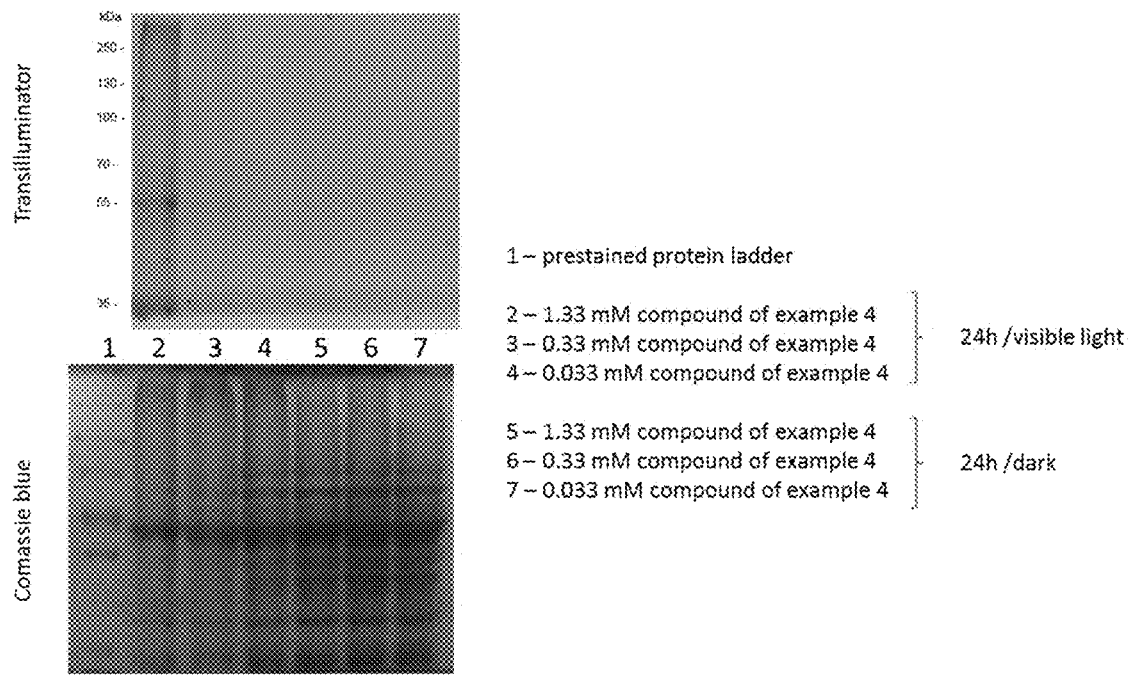

1 – prestained protein ladder

2 – 1.33 mM compound of example 4  
3 – 0.33 mM compound of example 4      24h /visible light  
4 – 0.033 mM compound of example 4

5 – 1.33 mM compound of example 4  
6 – 0.33 mM compound of example 4      24h /dark  
7 – 0.033 mM compound of example 4

Figure 3

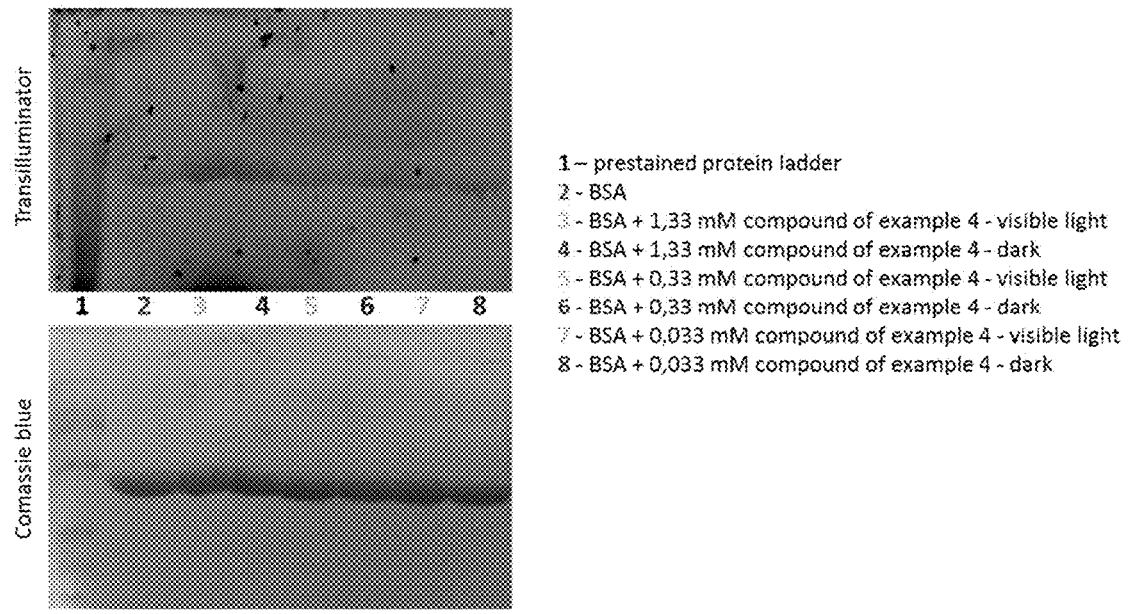

1 – prestained protein ladder  
2 – BSA  
3 – BSA + 1,33 mM compound of example 4 - visible light  
4 – BSA + 1,33 mM compound of example 4 - dark  
5 – BSA + 0,33 mM compound of example 4 - visible light  
6 – BSA + 0,33 mM compound of example 4 - dark  
7 – BSA + 0,033 mM compound of example 4 - visible light  
8 – BSA + 0,033 mM compound of example 4 - dark

QUINONE-METHIDE PRECURSORS WITH BODIPY CHROMOPHORE, METHOD OF PREPARATION, BIOLOGICAL ACTIVITY AND APPLICATION IN FLUORESCENT LABELLING

FIELD OF THE INVENTION

The invention relates to new series of quinonemethide precursors with BODIPY chromophore, methods of their preparation, transformation to quinone methides by use of light, their antiproliferative activity and use of the compounds presented herein for fluorescent labelling.

BACKGROUND OF THE INVENTION

BODIPY is an abbreviation for the IUPAC name for fluorescent dye 4,4-difluoro-4-bora-3a,4a-diaza-s-indacene. The first BODIPY derivative was synthesized by Treibs and Kreuzer in 1968 (A. Treibs, F.-H. Kreuzer, *Justus Liebigs Ann. Chem.* 1968, 718, 208-223). However, the interest in these derivatives was developed after 1980s when potential use of the dyes was found (F. J. Monsma, A. C. Barton, H. C. Kang, D. L. Brassard, R. P. Haughland, D. R. Sibley, *J. Neurochem.* 1989, 52, 1641-1644, EP 0 361 936 A2) and several BODIPY dyes were commercialized for biological labelling (U.S. Pat. No. 4,774,339, US 2005/0186641 A1, US 2010/0252433 A1).

Since then, BODIPY is a registered trademark of a company for molecular probes "Invitrogen", or nowadays "Lifetime technologies". BODIPY derivatives are characterized by good chemical and photochemical stability, good solubility in many solvents, excellent spectral and photophysical properties (relatively high molar absorption coefficients and fluorescence quantum yields, negligible triplet-state formation, narrow emission bandwidths with high peak intensities, resistance towards self-aggregation in solution, excitation/emission wavelengths in the visible spectral region, and fluorescence lifetimes in the nanosecond range). Furthermore, their spectral properties can be finely tuned by attachment of different residues at the appropriate positions. Consequently, a huge number of BODIPY derivatives has been synthesized and their spectroscopic and photophysical properties characterized, as well as their applicability in different biological aspects developed (G. Ulrich, R. Ziessel, A. Harriman, *Angew. Chem. Int. Ed.* 2008, 47, 1184-1201; A. Loudet, K. Burgess, *Chem. Rev.* 2007, 107, 4891-4893; N. Boens, V. Leen, W. Dehaen, *Chem. Soc. Rev.* 2012, 41, 1130-1172). In spite of a large number of BODIPY dyes available, there are only a few examples wherein their ability for binding to different analites and/or biomolecules was altered by photoactivation (E. Deniz, M. Battal, J. Cusido, S. Sortino, F. M. Raymo, *Phys. Chem. Chem. Phys.* 2012, 14, 10300-10307; S. S. Ragab, S. Swaminathan, E. Deniz, B. Capitan, F M. Raymo, *Org. Lett.* 2013, 15, 3154-3157; T. Aotake, M. Suzuki, D. Kuzuhara, N. Aratani, N. Tamai, H. Yamada, *Chem. Eur. J.* 2015, 21, 1-10), and none of them is based on photochemical formation of quinone methides (QMs).

QMs are reactive intermediates in chemistry and photochemistry of phenols exhibiting both electrophilic and nucleophilic character. In particular, it has been demonstrated that QMs react as electrophiles with different biomacromolecules enabling potential biological applications (M. Freccero, *Mini Rev. Org. Chem.* 2004, 1, 403-415; P. Wang, Y. Song, L. Zhang, H. He, X. Zhou, *Curr. Med. Chem.*, 2005, 12, 2893-2913). Thus, QMs react with amino acids (E. Modica, R. Zanaletti, M. Freccero, M. Melia, *J. Org. Chem.*, 2001, 66, 41-52), and proteins (S. Arumugam, J. Guo, N. E. Mbua, F. Fiscourt, N. Lin, E. Nekongo, G. J. Boons, V. V. Popik, *Chem. Sci.*, 2014, 5, 1591-1598), and affect action of some enzymes such as tyrosine hydroxylases, β-lactamase, β-glucosidases, phosphatase, or ribonuclease-A. Moreover, QMs react with nucleosides and facilitate alkylation and cross-linking of DNA. QM-naphthalimimide conjugates targeting guanine-quadruplex structures, as well as reversible DNA alkylation abilities of QMs has recently been demonstrated (H. Wang, *Curr. Org. Chem.* 2014, 18, 44-60). In general, reactivity of QMs with nucleic acids leads to the application of QMs as antineoplastic antibiotics with mitomycin as the most prominent example.

QMs can be formed in mild conditions in photochemical reactions (N. Basarić, K. Mlinarić-Majerski, M. Kralj, *Curr. Org. Chem.* 2014, 18, 3-18; C. Percivalle, F. Doria, M. Freccero, *Curr. Org. Chem.* 2014, 18, 19-43). Photochemistry is particularly applicable to biological systems since photoexcitation and formation of reactive species can be temporarily and spatially controlled, for example inside the living cell, with a pulsed laser beam. The most common photochemical reaction applied in the biological systems is photodehydration of appropriately substituted phenols or deamination of the corresponding Mannich bases or their salts (Đ. Škalamera, C. Bohne, S. Landgraf, N. Basarić, *J. Org. Chem.*, 2015, 80, 10817-10828. E. Modica, R. Zanaletti, M. Freccero, M. Mella, *J. Org. Chem.*, 2001, 66, 41-52). Photochemical formation of QMs has been explored and it has been demonstrated that it leads to enhanced antiproliferative activity on several human cancer cell lines (N. Basarić, N. Cindro, D. Bobinac, K. Mlinarić-Majerski, L. Uzelac, M. Kralj, P. Wan, *Photochem. Photobiol. Sci.*, 2011, 10, 1910-1925. N. Basarić, N. Cindro, D. Bobinac, L. Uzelac, K. Mlinarić-Majerski, M. Kralj, P. Wan, *Photochem. Photobiol. Sci.*, 2012, 11, 381-396. J. Veljković, L. Uzelac, K., Molčanov, K. Mlinarić-Majerski, M. Kralj, P. Wan, N. Basarić, *J. Org. Chem.*, 2012, 77, 4596-4610. Đ. Škalamera, K. Mlinarić-Majerski, I. Martin-Kleiner, M. Kralj, P. Wan, N. Basarić, *J. Org. Chem.* 2014, 79, 4390-4397. M. Kralj, L. Uzelac, Y.-H. Wang, P. Wan, M. Tireli, K. Mlinarić-Majerski, I. Piantanida, N. Basarić, *Photochem. Photobiol. Sci.*, 2015, 14, 1082-1092). Consequently, QM precursors can in principle be considered as pro-drugs that upon excitation by light are transferred to QMs—drugs that exert biological effect.

Formation of QMs from a precursor having chromophore absorbing in the visible part of the spectrum (>450 nm) has not yet been reported. Present invention relating to BODIPY-QM precursors represents a significant improvement since it enables formation of QMs by use of common light sources such as LEDs or lasers. Formation of QMs with the damaging cellular properties can be applied in the anticancer therapy, whereas non-cytotoxic derivatives have potential in intracellular labelling of biomacromolecules, nucleic acids and proteins in particular. In the previous reports, fluorescent groups were covalently attached to a naphthalene QM precursor absorbing at ≈350 nm (S. Arumugam, V. V. Popik, *J. Am. Chem. Soc.* 2011, 133, 15730-15736. S. Arumugam, V. V. Popik, *J. Am. Chem. Soc.* 2012, 134, 8408-8411).

QM-precursors with a BODIPY structure have not yet been reported. Some similar molecules were described in the literature as sensors of inorganic cations (I.-S. Shin, S. W. Bae, H. Kim, J.-I. Hong, *Anal. Chem.* 2010, 82, 8259-8265. S. W. Bae, E. Kim, I.-S. Shin, S. B. Park, J.-I. Hong,

*Supramol. Chem.* 2013, 25, 2-6. D. P. Murale, S. T. Manjare, Y.-S. Lee, D. G. Churchill, *Chem. Commun.* 2014, 50, 359-361), but they were not used in the photochemical reactions for the formation of QMs nor their potential in the therapy or biolabelling have been demonstrated.

The use of BODIPY dyes in the treatment of neoplastic diseases (EP 0 361 936 A2) has been based on the sensitization of oxygen and cytotoxic activity of singlet oxygen, known as photodynamic therapy. The use of BODIPY dyes described herein in the treatment of cancer is based on the formation of QMs, so it has many advantages over the previous method, primarily in the hypoxic tissues, and potential selectivity towards cancer stem cells. Moreover, the use of BODIPY dyes for biological labelling (U.S. Pat. No. 4,774,339, US 2005/0186641 A1, US 2010/0252433 A1) has not been based on the photoactivation, so the current report present a significant breakthrough in the current state of the art since it can be accomplished inside of the living cells.

SUMMARY OF THE INVENTION

The present invention relates to BODIPY derivatives represented by Formula (I):

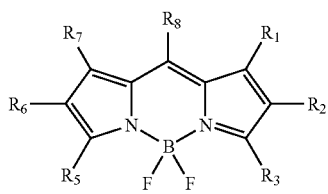

I wherein
$R^1$, $R^2$, $R^6$ and $R^7$ are independently selected from H, Cl, Br and $C_1$-$C_4$ alkyl;
$R^3$ and $R^5$ are independently selected from H, Cl, Br, $C_1$-$C_4$ alkyl, aryl, —CH=CH-aryl, A and —CH=CH-A;
$R^8$ is selected from aryl and A;
wherein aryl may be unsubstituted or substituted by 1-3 substituents selected from $C_1$-$C_4$ alkyl, $C_1$-$C_4$ haloalkyl, $C_1$-$C_4$ alkoxy, and OH;
A is a substituent of formula:

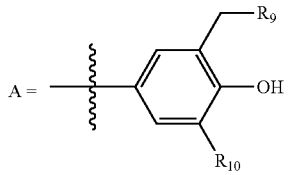

$R^9$ is selected from —N($C_1$-$C_4$ alkyl)$_2$, —N($C_1$-$C_4$ alkyl)$_2$H$^+$X$^-$ and —N($C_1$-$C_4$ alkyl)$_3$$^+$X$^-$,
X$^-$ is Cl$^-$ Br$^-$, or I$^-$;
$R^{10}$ is selected from H and —CH$_2$R$^9$;
with the proviso that at least one of $R^3$, $R^5$ and $R^8$ is A or one of $R_3$ and $R_5$ is —CH=CH-A;
or a salt thereof.

The present invention also relates to pharmaceutical compositions comprising a compound of Formula (I) or a pharmaceutically acceptable salt thereof.

Furthermore, the present invention relates to a compound of Formula (I) or a pharmaceutically acceptable salt thereof for use in human or veterinary medical therapy.

In another aspect, the invention relates to a compound of Formula (I) for use in the antiproliferative treatment.

In further aspect the present invention relates to a compound of Formula (I) for use in fluorescent labelling of proteins, or nucleic acids.

BRIEF DESCRIPTION OF THE FIGURES

FIG. 2. Labelling of total cell lysates with compound of example 4. 50 µg of total cell lysate was incubated with indicated concentrations of BODIPY on ice in dark or exposed to visible light. The lysates incubated with compound of Example 4 were then resolved on SDS-PAGE. The labelled proteins were visualised in gel using UV transilluminator and upon that stained with Comassie blue stain.

FIG. 3. Labelling of BSA with compound of example 4. 10 µg of BSA was incubated without test compound or with indicated concentrations of compound of Example 4 on ice in dark or exposed to visible light. The BSA incubated with compound of Example 4 was then subjected to SDS-PAGE. The labelled BSA was visualised in gel using UV transilluminator and upon that stained with Comassie blue stain.

DETAILED DESCRIPTION OF THE INVENTION

Figure 1:
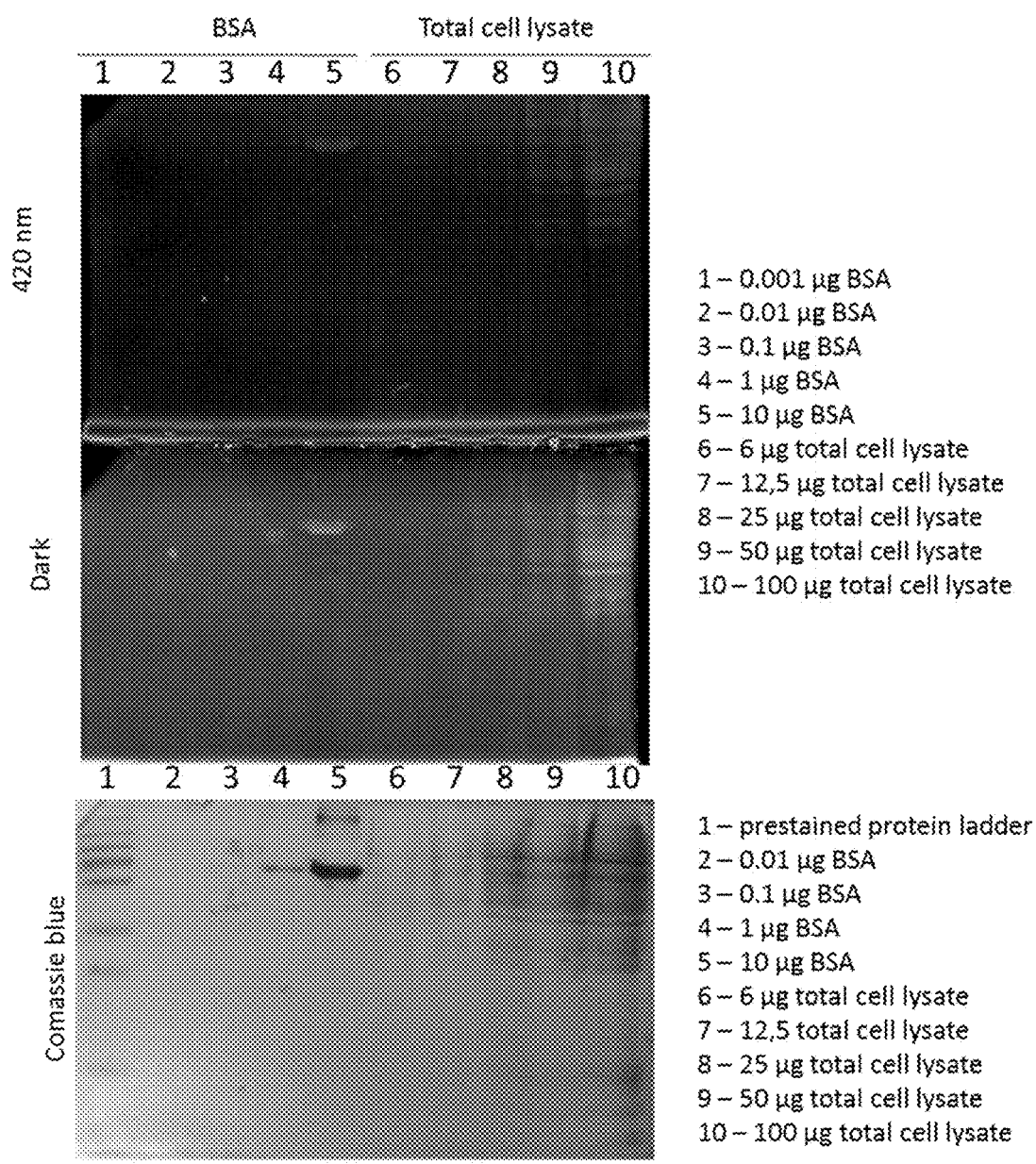
FIG. 1. Labelling of proteins resolved on SDS-PAGE with compound of example 4. Indicated concentrations of BSA or total cell lysate were resolved on SDS-PAGE. The gels with resolved proteins were subsequently incubated in 1.33 mM compound of Example 4 diluted in PBS in dark or irradiated with 450 nm light. The labelled proteins were visualised using UV transilluminator. Additionally, the same concentrations of BSA or total cell lysate were resolved on SDS-PAGE and stained with 0.1% Coomassie blue.

It will be understood that the present invention covers all combinations of aspects, suitable, convenient and preferred groups described herein.

References hereinafter to "a compound of the invention" or "compounds of the present invention" or a BODIPY of Formula (I) include both a compound of Formula (I) and its salts. In one aspect it includes compounds of Formula (I) or its pharmaceutically acceptable salts. The compounds of the present invention may exist as geometric cis/trans isomers. The present invention includes the individual geometric isomers of the compounds of the invention and, where appropriate mixtures thereof.

In the context of the present invention, the substituents, if not stated otherwise, in general have the following meaning:

The term "alkyl" as used herein, refers to a saturated, straight or branched-chain hydrocarbon radical containing the stated number of carbon atoms. For example, "$C_1$-$C_4$ alkyl" contains between one and four carbon atoms. Examples of "$C_1$-$C_4$ alkyl" radicals include: methyl, ethyl, n-propyl, isopropyl, n-butyl, isobutyl, sec-butyl and tert-butyl.

The term "alkoxy" as used herein, refers to an —O-alkyl group wherein alkyl is as defined above. Examples of "—$C_1$-$C_4$ alkoxy" radicals include: methoxy, ethoxy, propoxy, isopropoxy, n-butoxy, isobutoxy, sec-butoxy, tert-butoxy, and the like.

The term "—$C_1$-$C_4$ haloalkyl" as used herein, refers to straight or branched alkyl containing the stated number of carbon atoms and having one or more hydrogens substituted by a halogen selected from bromo, chloro, fluoro or iodo. Examples of such groups include trifluoromethyl, 2,2,2-trifluorethyl, 2-fluorethyl and the like.

The term "aryl" as used herein refers to a $C_6$-$C_{10}$ monocyclic or bicyclic hydrocarbon ring wherein at least one ring is aromatic. Examples of such groups include phenyl, naphthyl, tetrahydronaphthyl and the like.

The term "heteroaryl" as used herein refers to 5-6 membered monocyclic or 9-10 membered bicyclic aromatic ring containing 1-2 heteroatoms independently selected from oxygen, nitrogen and sulphur. Examples of such monocyclic rings include furyl, pyrrolyl, thienyl, imidazolyl, pyrazolyl, oxazolyl, isoxazolyl, thiazolyl, pyridinyl, pyrazinyl, pyrimidinyl, pyridazinyl and the like. Examples of such bicyclic rings include benzofuryl, indolyl, benzothienyl, benzimidazolyl, indazolyl, benzoxazolyl, benzothiazolyl, quinolinyl, quinoxalinyl, quinazolinyl, and the like.

The term "irradiating" or "use of light" as used herein refers to photochemical excitation of compounds of formula (I) by use of light of appropriate wavelength that compound can absorb and different light sources including lamps, LED, lasers, optical fibres, etc.

"Subject" refers to an animal, in particular a mammal and more particularly to a human or a domestic animal or an animal serving as a model for a disease (e.g., mouse, monkey, etc.). In one aspect, the subject is a human.

A "therapeutically effective amount" means the amount of a compound that, when administered to a subject for treating a cancer is sufficient to effect such treatment. The "therapeutically effective amount" will vary depending on the severity of the disease, the age, weight, physical condition and responsiveness of the subject to be treated and will ultimately be at the discretion of the attendant physician.

"Treating" or "treatment" of cancer means the alleviation of the symptoms and/or retardation of progression of the disease, and may include the suppression of symptom recurrence in an asymptomatic patient.

In one aspect the present invention relates to a compound of Formula (I) or a salt thereof wherein the salt is a pharmaceutically acceptable salt. Suitable pharmaceutically acceptable salts can include acid or base addition salts.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartarte, citrate, formate, gluconate, succinate, salicylate, propionate, pyruvate, hexanoate, oxalate, oxaloacetate, trifluoroacetate, saccharate, glutamate, aspartate, benzoate, alkyl or aryl sulphonates (e.g. methanesulphonate, ethanesulphonate, benzenesulphonate or p-toluenesulphonate), triflate, isethionate and the like.

Many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The salts of compounds of Formula (I) may form solvates (e.g. hydrates) and the invention also includes all such solvates.

In one aspect, compounds of the present invention may be in the form of pharmaceutically acceptable salts, solvates or solvates of salts. In a further aspect, a compound of Formula (I) of the present invention may be in the form of a pharmaceutically acceptable salt.

In one aspect, the present invention relates to the compounds of Formula (I) wherein $R^1$, $R^2$, $R^6$ and $R^7$ are independently selected from H and $C_1$-$C_4$ alkyl. In a further aspect $R^1$, $R^2$, $R^6$ and $R^7$ are independently selected from H and methyl. In a further aspect $R^1$, $R^2$, $R^6$ and $R^7$ are all hydrogen. In yet further aspect $R^1$, $R^3$, $R^5$ and $R^7$ are methyl wherein $R^2$ and $R^6$ are hydrogen.

In one aspect of the invention $R^8$ is A.

In one aspect of the invention $R^8$ is A wherein $R^9$ is —N($C_1$-$C_4$ alkyl)$_2$H$^+$X$^-$ and $R^{10}$ is H. In a further aspect $R^8$ is A wherein $R^9$ is —N(CH$_3$)$_2$H$^+$Cl$^-$ and $R^{10}$ is H. In yet a further aspect $R^8$ is A wherein $R^9$ is —N(CH$_3$)$_2$H$^+$Cl$^-$ and $R^{10}$ is CH$_2$R$^9$.

In one aspect of the invention $R^3$ is A wherein $R^9$ is —N($C_1$-$C_4$ alkyl)$_2$H$^+$X$^-$ and $R^{10}$ is H. In a further aspect $R^8$ is A wherein $R^9$ is —N(CH$_3$)$_2$H$^+$Cl$^-$ and $R^{10}$ is H. In yet a further aspect $R^3$ is A wherein $R^9$ is —N(CH$_3$)$_2$H$^+$Cl$^-$ and $R^{10}$ is CH$_2$R$^9$.

In one aspect of the invention $R^3$ is —CH=CH-A.

In one aspect of the invention $R^3$ is —CH=CH-A wherein $R^9$ is —N($C_1$-$C_4$ alkyl)$_2$H$^+$X$^-$ and $R^{10}$ is H. In a further aspect $R^3$ is —CH=CH-A wherein $R^9$ is —N(CH$_3$)$_2$H$^+$Cl$^-$ and $R^{10}$ is H. In yet a further aspect $R^3$ is —CH=CH-A wherein $R^9$ is —N(CH$_3$)$_2$H$^+$Cl$^-$ and $R^{10}$ is CH$_2$R$^9$.

In one aspect of the invention $R^3$ and $R^8$ are both A.

In one aspect of the invention $R^3$ and $R^8$ are A wherein $R^9$ is —N($C_1$-$C_4$ alkyl)$_2$H$^+$X$^-$ and $R^{10}$ is H. In a further aspect $R^3$ and $R^8$ are A wherein $R^9$ is —N(CH$_3$)$_2$H$^+$Cl$^-$ and $R^{10}$ is H. In yet a further aspect $R^3$ and $R^8$ are A wherein $R^9$ is —N(CH$_3$)$_2$H$^+$Cl$^-$ and $R^{10}$ is CH$_2$R$^9$.

In one aspect of the invention $R^3$ and $R^5$ are independently selected from H, Cl, Br, $C_1$-$C_4$ alkyl, aryl, —CH=CH-aryl, A and —CH=CH-A.

In one aspect of the invention $R^3$ and $R^5$ are both A.

In one aspect of the invention $R^3$ and $R^5$ are A wherein $R^9$ is —N($C_1$-$C_4$ alkyl)$_2$H$^+$X$^-$ and $R^{10}$ is H. In a further aspect $R^3$ and $R^5$ are A wherein $R^9$ is —N(CH$_3$)$_2$H$^+$Cl$^-$ and $R^{10}$ is H. In yet a further aspect $R^3$ and $R^5$ are A wherein $R^9$ is —N(CH$_3$)$_2$H$^+$Cl$^-$ and $R^{10}$ is CH$_2$R$^9$.

In one aspect of the invention $R^3$ and $R^5$ are both —CH=CH-A.

In one aspect of the invention $R^3$ and $R^5$ are —CH=CH-A wherein $R^9$ is —N($C_1$-$C_4$ alkyl)$_2$H$^+$X$^-$ and $R^{10}$ is H. In a further aspect $R^3$ and $R^5$ are —CH=CH-A wherein $R^9$ is —N(CH$_3$)$_2$H$^+$Cl$^-$ and $R^{10}$ is H. In yet a further aspect $R^3$ and $R^5$ are —CH=CH-A wherein $R^9$ is —N(CH$_3$)$_2$H$^+$C$^-$ and $R^{10}$ is CH$_2$R$^9$.

In one aspect of the invention $R^8$ is A wherein $R^3$ and $R^5$ are independently selected from H, Cl, Br, $C_1$-$C_4$ alkyl, $C_1$-$C_4$ alkoxy, aryl. In a further aspect $R^8$ is A wherein $R^3$ and $R^5$ are independently selected from H, and $C_1$-$C_4$ alkyl, A, CH=CH-A.

In one aspect of the invention $R^3$ is A wherein $R^5$ is selected from H, Cl, Br, $C_1$-$C_4$ alkyl, $C_1$-$C_4$ alkoxy, aryl, and $R^8$ is aryl, preferably phenyl.

In one aspect of the invention $R^3$ is —CH=CH-A wherein $R^5$ is selected from H, Cl, Br, $C_1$-$C_4$ alkyl, $C_1$-$C_4$ alkoxy, aryl, and $R^8$ is aryl, preferably phenyl.

Compounds of the Formula (I) include:

4,4-Difluoro-8-[3-(N,N-dimethylaminomethyl)-4-hydroxyphenyl]-4-bora-3a,4a-diaza-s-indacene;

4,4-Difluoro-8-[3-(N,N-dimethylammoniummethyl)-4-hydroxyphenyl]-4-bora-3a,4a-diaza-s-indacene hydrochloride;

4,4-Difluoro-1,3,5,7-tetramethyl-8-[3-(N,N-dimethylaminomethyl)-4-hydroxyphenyl]-4-bora-3a,4a-diaza-s-indacene;

4,4-Difluoro-1,3,5,7-tetramethyl-8-[3-(N,N-dimethylammoniummethyl)-4-hydroxyphenyl]-4-bora-3a,4a-diaza-s-indacene hydrochloride;

4,4-Difluoro-1,3,5,7-tetramethyl-8-[3,5-bis(N,N-dimethylammonium-methyl)-4-hydroxyphenyl]-4-bora-3a,4a-diaza-s-indacene hydrochloride;

4,4-Difluoro-1,5,7-trimethyl-3-{2-[3-(N,N-dimethylaminomethyl)-4-hydroxyphenyl]ethenyl}-8-phenyl-4-bora-3a,4a-diaza-s-indacene;

4,4-Difluoro-1,5,7-trimethyl-3-[3-(N,N-dimethylammoniummethyl)-4-hydroxyphenyl]-8-phenyl-4-bora-3a,4a-diaza-s-indacene hydrochloride;

4,4-Difluoro-3-[3-(N,N-dimethylaminomethyl)-4-hydroxyphenyl]-8-phenyl-4-bora-3a,4a-diaza-s-indacene;

4,4-Difluoro-3-chloro-5-[3-(N,N-dimethylaminomethyl)-4-hydroxyphenyl]-8-phenyl-4-bora-3a,4a-diaza-s-indacene;

4,4-Difluoro-3,5-dichloro-8-[3-(N,N-dimethylaminomethyl)-4-hydroxyphenyl]-4-bora-3a,4a-diaza-s-indacene;

4,4-Difluoro-3,5-bis[3-(N,N-dimethylaminomethyl)-4-hydroxyphenyl]-8-phenyl-4-bora-3a,4a-diaza-s-indacene;

4,4-Difluoro-1,7-dimethyl-3,5-bis{2-[3-(N,N-dimethylaminomethyl)-4-hydroxyphenyl]ethenyl}-8-phenyl-4-bora-3a,4a-diaza-s-indacene.

In one aspect present invention relates to compounds represented by Formula (I):

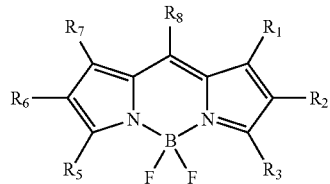

I wherein $R^1$, $R^2$, $R^6$ and $R^7$ are independently selected from H and $CH_3$;

$R^3$ and $R^5$ are independently selected from H, Cl, $CH_3$, aryl, —CH=CH-aryl, A and —CH=CH-A; wherein aryl is unsubstituted or substituted by OH;

$R^8$ is selected from phenyl and A

A is a substituent of formula:

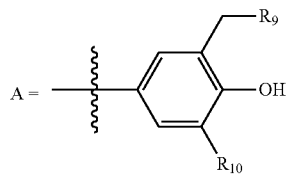

$R^9$ is selected from —N(CH$_3$)$_2$—N(CH$_3$)$_2$H$^+$Cl$^-$;

$R^{10}$ is selected from H and —CH$_2$R$^9$;

with the proviso that at least one of $R^3$, $R^5$ and $R^8$ is A or —CH=CH-A;

or a salt thereof.

In one aspect the present invention relates to compounds of Formula (IB)

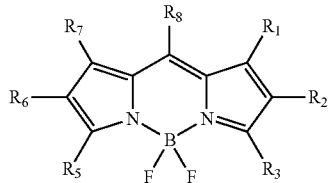

1B wherein $R^1$, $R^2$, $R^6$ and $R^7$ are independently selected from H, Cl, Br, $C_1$-$C_4$ alkyl and phenyl; wherein phenyl may be unsubstituted or substituted by 1-3 substituents selected from $C_1$-$C_4$ alkyl, $C_1$-$C_4$ haloalkyl and $C_1$-$C_4$ alkoxy;

$R^3$ and $R^5$ are independently selected from H, Cl, Br, $C_1$-$C_4$ alkyl, $C_1$-$C_4$ alkoxy, aryl, arylamine, heteroaryl, A and —CH=CH-A;

$R^8$ is selected from H, $C_1$-$C_4$ alkyl, CF$_3$, aryl, heteroaryl, A and —CH=CH-A;

wherein aryl and heteroaryl may be unsubstituted or substituted by 1-3 substituents selected from $C_1$-$C_4$ alkyl, $C_1$-$C_4$ haloalkyl, $C_1$-$C_4$ alkoxy and OH;

A is a substituent of formula:

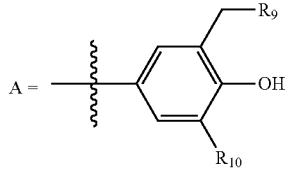

$R^9$ is selected from —N($C_1$-$C_4$ alkyl)$_2$, —N($C_1$-$C_4$ alkyl)$_2$H$^+$X$^-$ and —N($C_1$-$C_4$ alkyl)$_3$$^+$X$^-$, X$^-$ is Cl$^-$Br$^-$, or I$^-$;

$R^{10}$ is selected from H and —CH$_2$R$^9$;

with the proviso that at least one of $R^3$, $R^5$ and $R^8$ is A or —CH=CH-A; or a salt thereof.

Compounds of the present invention may be easily transformed to quinone methide (QM) derivatives of formula 1A bellow by use of light.

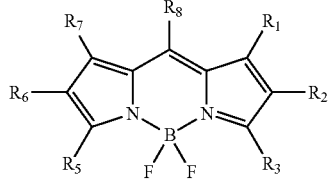

1A wherein at least one of $R^3$, $R^5$ and $R^8$ is A" or —CH=CH-A" and

A" is a group of formula:

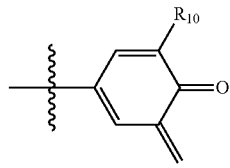

Use of QMs as Antiproliferative Agent

Quinone methide derivatives (QMs) are known as DNA alkylating agents (H. Wang, Curr. Org. Chem. 2014, 18, 44-60). The DNA damage induced by alkylation stops cell proliferation, making these compounds a cytostatic drug (K. Brandt, R. Kruszynksi, T. J. Bartczak, I. Porwolik-Czomperlik, Inorg. Chim. Acta 2001, 322, 138-144).

Compounds of the present invention inhibit the cell proliferation after exposing to the light. Therefore, these compounds may have utility in the treatment of cancer.

The advantage of the treatment with compounds of the present invention is that active QMs are generated in situ at the desired places by use of light. In that way side effects of therapy can be minimized since cancer tissue can be irradiated selectively.

In one aspect, the present invention provides a method of treating cancer in a subject in need of such treatment comprising administering to the subject a therapeutically effective amount of a compound of formula (I) or a pharmaceutically acceptable salt thereof and subsequently irradiating the subject in need thereof to form an active QMs derivative in situ.

In one aspect, the present invention provides a compound of Formula (I) or a pharmaceutically acceptable salt thereof for use in medical therapy.

In one aspect, the present invention provides a compound of Formula (I) or a pharmaceutically acceptable salt thereof, for use in the treatment of cancer.

In a further aspect, the present invention provides the use of a compound of Formula (I) or a pharmaceutically acceptable salt thereof in the manufacture of a medicament for the treatment of cancer.

Use of QMs as Fluorescent Labelling Reagent

In one aspect, the present invention provides a compound of Formula (I) or a salt thereof for use as fluorescent labelling reagent.

In one aspect, the present invention provides a methods for detecting a protein or a group of protein comprising the following steps:

(a) contacting/incubating a protein or a mixture of proteins with a compound of Formula (I) or a salt thereof while irradiating the mixture with appropriate wavelength that a compound of Formula (I) can absorb;

(b) subjecting a mixture from step (a) to gel electrophoresis;

(c) detecting fluorescence.

In one aspect, the present invention provides a method of visualizing a protein bound, said method comprising:

(a) subjecting a protein or a mixture of proteins to gel electrophoresis;

(b) incubating the gel from step (a) with solution containing a compound of Formula (I) or a salt thereof;

(c) irradiating the gel from step (b) with appropriate wavelength that a compound of Formula (I) can absorb;

(d) detecting the fluorescence

In one aspect, the present invention provides a method of visualizing a protein bound, said method comprising:

(a) subjecting a protein or a mixture of proteins to gel electrophoresis wherein the gel comprises a compound of Formula (I) or a salt thereof;

(c) irradiating the gel after the gel electrophoresis with appropriate wavelength that a compound of Formula (I) or a salt thereof—protein complex can absorb;

(d) detecting an fluorescence.

Pharmaceutical Compositions

While it is possible that, for use in the methods of the invention, a compound of Formula (I) or a pharmaceutically acceptable salt thereof may be administered as the bulk substance, it is preferable to present the active ingredient in a pharmaceutical formulation, for example, wherein the agent is in admixture with at least one pharmaceutically acceptable carrier selected with regard to the intended route of administration and standard pharmaceutical practice.

Accordingly, the present invention provides a pharmaceutical composition comprising:

a) a compound of Formula (I) or a pharmaceutically acceptable salt thereof and b) one or more pharmaceutically acceptable carriers.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

Pharmaceutical compositions may be presented in unit dose forms containing a predetermined amount of active ingredient per unit dose. As is known to those skilled in the art, the amount of active ingredient per dose will depend on the condition being treated, the route of administration and the age, weight and condition of the patient.

It will be appreciated that pharmaceutical compositions for use in accordance with the present invention may be in the form of oral, parenteral, transdermal, sublingual, topical, implant, nasal, or enterally administered (or other mucosally administered) suspensions, capsules or tablets, which may be formulated in conventional manner using one or more pharmaceutically acceptable carriers or excipients.

Method of Preparation:

Compounds of Formula (I) and salts thereof may be prepared by the general methods outlined hereinafter, said methods constituting a further aspect of the invention. In the following description, the groups A, $R^1$, $R^2$, $R^3$, $R^4$, $R^5$, $R^6$, $R^7$, $R^8$, $R^9$ and $R^{10}$ have the meaning defined for the compounds of Formula (I) unless otherwise stated.

Compounds of Formula (I) wherein $R^9$ is —$N(C_1$-$C_4$ alkyl$)_2$ and $R^{10}$=H may be prepared by reaction of the corresponding phenol derivatives of Formula (II)

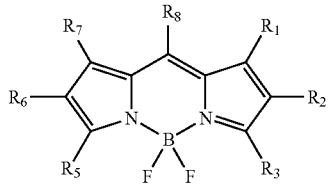

wherein at least one of $R^3$, $R^5$ and $R^8$ is A' or —CH=CH-A; and

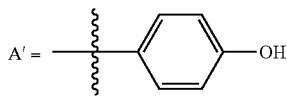 [SMILES: *c1ccc(O)cc1]

with Mannich reagent, that is commercially available or is prepared in situ wherein the molar ratio of the starting compound of Formula (II) and the Mannich reagent is 1:1 to 1:2.

The reaction involves mixing of compound of Formula (II) and Mannich reagent prepared from formaldehde and the corresponding dialkylamine (dimethylamine, diethylamine, dipropylamine, di-i-propilamine, dibutylamine or the like) in aqueous or other solvent selected from halogenated solvents, ethers, hydrocarbons or alcohols. The reaction is carried out at room temperature or elevated temperatures up to 100° C. over 1 h up to seven days. The product, in organic solvents, is removed from inorganic salts by filtration, or by extractions. The solvents for the extractions may be selected from esters, ethers, halogenated solvents or hydrocarbons. After drying of the organic solvents with anhydrous salts such as $Na_2SO_4$, $MgSO_4$, $K_2CO_3$ or $CaCl_2$ and removal of the solvent the product of formula (I) is purified on $Al_2O_3$ or by crystallization using esters, ethers, halogenated solvents, nitriles or hydrocarbons as solvent.

Compounds of Formula (I) wherein $R^9$ is —N($C_1$-$C_4$ alkyl)$_2$ and $R^{10}$ is $CH_2R^9$ may be prepared by the reaction described above for the synthesis of compounds of Formula (I) wherein $R^9$ is —N($C_1$-$C_4$ alkyl)$_2$ and $R^{10}$ is H with the difference that the excess of at least 10 equivalents of Mannich reagent prepared in situ is used.

Specifically for the compounds of Formula (I) wherein $R^9$ is —N($CH_3$)$_2$ and $R^{10}$=H or $CH_2R^9$ may be prepared by reaction of the corresponding phenol derivatives of Formula (II) as shown above with the Eschenmoser's salt $(CH_3)_2N^+CH_2$, in the presence of inorganic bases such as carbonates or hydroxides in anhydrous solvent selected from halogenated solvents, ethers, or hydrocarbons.

Compounds of Formula (I) wherein $R^9$ is —N($C_1$-$C_4$ alkyl)$_2$HX$^-$ can be prepared from compound of formula (I) wherein $R^9$ is —N($C_1$-$C_4$ alkyl)$_2$ and HX. The reaction is carried out by dissolving (I) in ethereal solvents and addition of HX dissolved in ethereal solvent, or by purging HX gas through ethereal solution of compound of Formula (I). The reaction yields crystals which are removed by filtration and washed with different solvents such as ethers and ketones.

Compounds of Formula (I) wherein $R^9$ is —N($C_1$-$C_4$ alkyl)$_3$X$^-$ can be prepared from compound of formula (I) wherein $R^9$ is —N($C_1$-$C_4$ alkyl)$_2$ and alkylhalogenide. The reaction is carried out by dissolving (I) in solvent comprising of ethers or amides such as DMF with alkylhalogenide in the presence of inorganic base such as carbonates or hydroxides. The reaction is carried out at room temperature or elevated temperatures up to 100° C. over 1 h up to seven days. After the reaction is completed the product of formula (I) is filtered or solvent is removed by evaporation and the crude product purified by washing with different solvents such as ethers, esters and ketones.

Compound of Formula (II) wherein $R^8$=A' or $R^8$=—CH=CH-A' may be prepared starting from pyrrole intermediate III and aldehyde IV wherein $R^8$ is A' or —CH=CH-A' which are converted to dipyrromethane under acidic conditions followed by oxidation with DDQ, chloranil or a similar reagent and complexation with $BF_3$ according to the known procedures (M. Baruah, W. Qin, N. Basarić, W. M. De Borggraeve and N. Boens, *J. Org. Chem.*, 2005, 70, 4152-4157) shown in the scheme below:

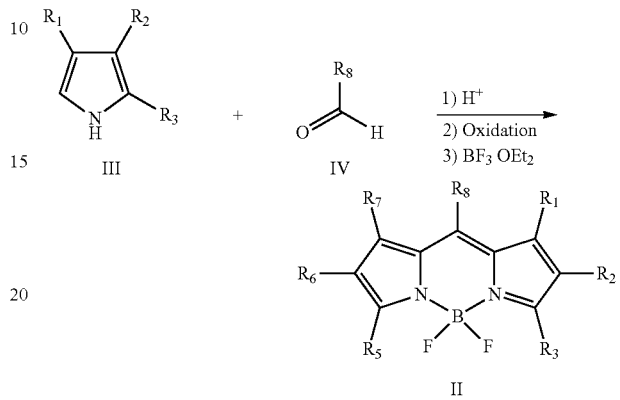

Specifically, for the preparation of compound of Formula (II) wherein $R^8$=A' or $R^8$=—CH=CH-A' and $R^3$ and $R^5$ are not the same, or $R^2$ and $R^6$ are not the same or $R^1$ and $R^7$ are not the same, a modified procedure is applied wherein one pyrrole substituted with $R^1$-$R^3$ is acylated first with $CF_3COCl$, and after reduction, the second pyrrole moiety substituted with $R^5$-$R^7$ is introduced (L. N. Sobenina, A. M. Vasil'tsov, O. V. Petrova, K. B. Petrushenko, I. A. Ushakov, G. Clavier, R. Mallet-Renault, A. I. Mikhaleva, B. A. Trofimov, *Org. Lett.* 2011, 13, 2524-2527) followed by oxidation and complexation with $BF_3$.

Further specifically, compound of Formula (II) wherein $R^8$=A' or $R^8$=—CH=CH-A', and all $R^1$-$R^7$=aryl can be prepared by bromination of pyrrole followed by introduction of three aryl groups in Suzuki coupling (V. Lakshmi, M. Ravikanth, *J. Org. Chem.* 2011, 76, 8466-8471). Condensation to dipyrromethane, oxidation and complexation with $BF_3$ gives compound of formula II.

Alternatively, compound of Formula (II) wherein $R^8$=A' or $R^8$=—CH=CH-A' and $R^3$=Aryl, or $R^5$=Aryl or $R^3$=$R^5$=Aryl, can be prepared from intermediate V

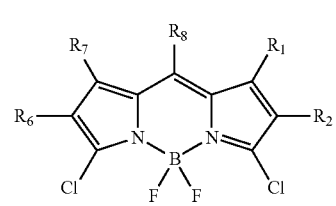

(M. Baruah, W. Qin, N. Basarić, W. M. De Borggraeve and N. Boens, *J. Org. Chem.*, 2005, 70, 4152-4157) by introducing aryl groups to $R^3$, and/or $R^5$ in Pd-catalyzed reaction (T. Rohand, W. Qin, N. Boens, W. Dehaen, *Eur. J. Org. Chem.* 2006, 4658-4663).

Compound of Formula (II) wherein $R^8$=A' or $R^8$=—CH=CH-A' and $R^3$=alkoxy or arylamine, or $R^5$=alkoxy or arylamine, or $R^3$=$R^5$=alkoxy or arylamine, can be prepared starting from intermediate V wherein $R^8$=A' or $R^8$=—CH=CH-A' (M. Baruah, W. Qin, N. Basarić, W. M. De Borggraeve and N. Boens, *J. Org. Chem.*, 2005, 70, 4152-4157) by nucleophilic substitution of chlorine by alkoxide or arylamine (T. Rohand, M. Baruah, W. Qin, N. Boens, W. Dehaen, *Chem. Commun.* 2006, 266-268).

Compound of Formula (II) wherein $R^3=R^5=A'$ can be prepared according to the known procedures shown in the scheme below:

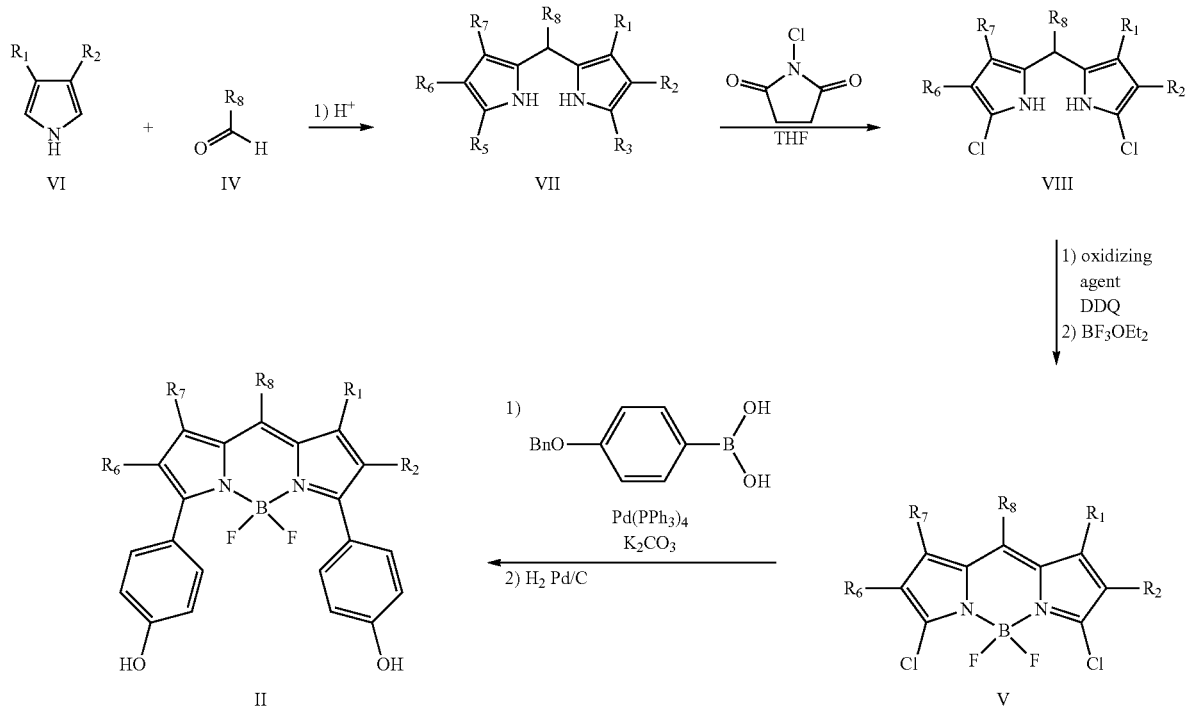

In the first step starting from the corresponding pyrrole precursor VI, condensation with aldehyde IV is carried out, followed by chlorination using N-chlorosuccinimide to afford VIII. Oxidation and complexation with $BF_3$ gives intermediate V (M. Baruah, W. Qin, N. Basarić, W. M. De Borggraeve and N. Boens, *J. Org. Chem.*, 2005, 70, 4152-4157) which can be arylated in a Suzuki reaction (T. Rohand, W. Qin, N. Boens, W. Dehaen, *Eur. J. Org. Chem.* 2006, 4658-4663) to intermediate from which the benzyl group on the aryl introduced in the Suzuki reaction can be cleaved off in the hydrogenation reaction (Đ. Škalamera, K. Mlinarić-Majerski, L. Uzelac, M. Kralj, P. Wan, N. Basarić, *Photochem. Photobiol. Sci.* 2013, 12, 2043-2056).

Compound of Formula (II) wherein $R^3=A'$ or $R^5=A'$ can be prepared from intermediate V according to the known procedures shown in the scheme below:

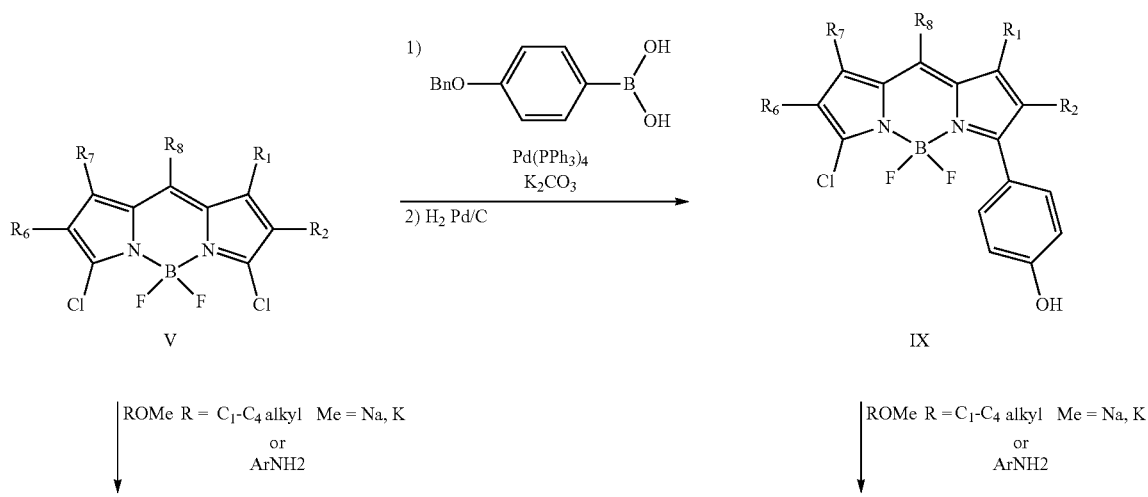

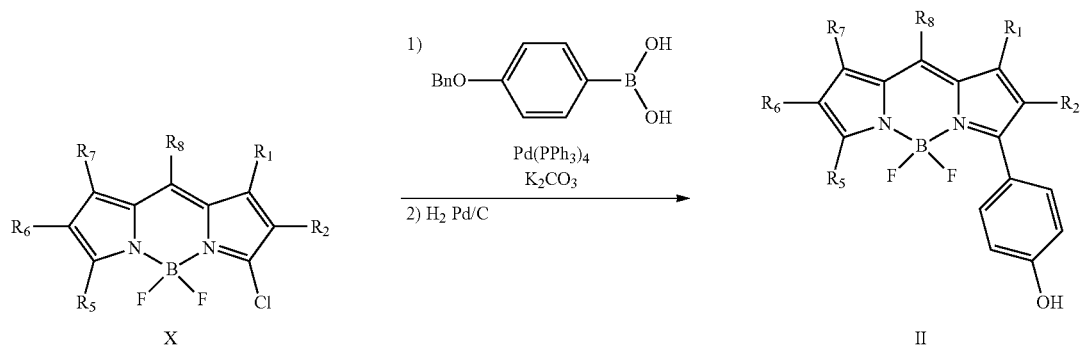

In the first step intermediate V reacts in the Suzuki coupling reaction (T. Rohand, W. Qin, N. Boens, W. Dehaen, *Eur. J. Org. Chem.* 2006, 4658-4663) to yield arylated intermediate from which the benzyl group is cleaved to afford IX. In the next step nucleophilic substitution with alkoxyde or arylamine gives II (T. Rohand, M. Baruah, W. Qin, N. Boens, W. Dehaen, *Chem. Commun.* 2006, 266-268). Alternatively, BODIPY intermediate V can react first in the nucleophilic substitution to afford X, and then arylation and subsequent benzyl group cleavage gives compound of Formula (II).

Compound of Formula (II) wherein $R^3$=A', $R^2$ and $R^6$ are not the same or $R^1$ and $R^7$ are not the same can be prepared according to the known procedures shown in the scheme below:

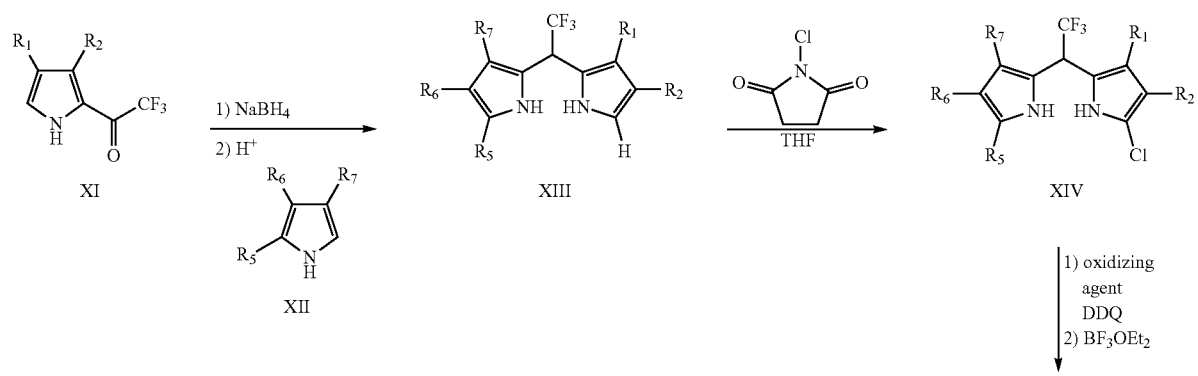

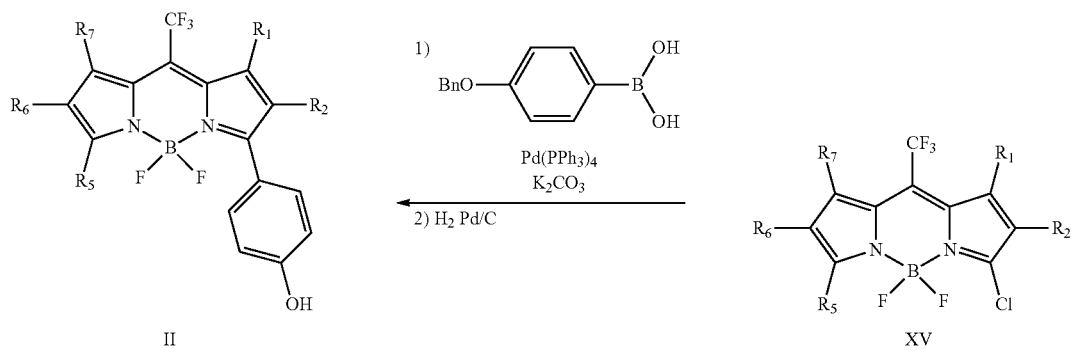

In the first step modified dipyrromethane XIII is prepared first from pyrrole precursors XI and XII (L. N. Sobenina, A. M. Vasil'tsov, O. V. Petrova, K. B. Petrushenko, I. A. Ushakov, G. Clavier, R. Mallet-Renault, A. I. Mikhaleva, B. A. Trofimov, *Org. Lett.* 2011, 13, 2524-2527). Subsequent chlorination, oxidation, and complexation with BF$_3$ affords BODIPY intermediate XV. Suzuki reaction and ether cleavage affords compound of Formula (II).

Compound of Formula (II) wherein $R^5$=A', $R^2$ and $R^6$ are not the same or $R^1$ and $R^7$ are not the same can be prepared according to the known procedures shown in the scheme above but starting from pyrrole precursors III and XVI:

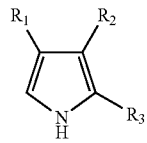

III

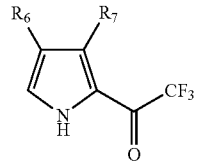

XVI

Compound of Formula (II) wherein $R^3$=—CH=CH-A', or $R^5$=—CH=CH-A' or $R^3$=$R^5$=—CH=CH-A' can be prepared according to the scheme below:

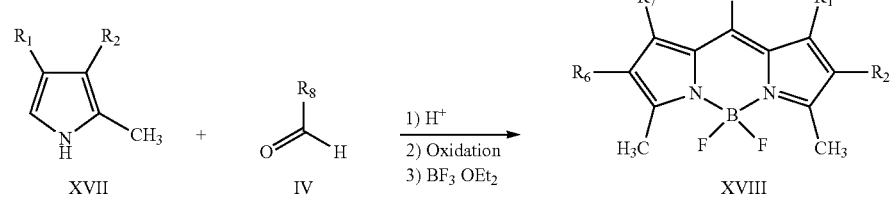

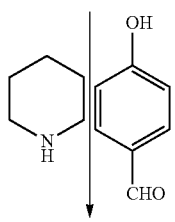

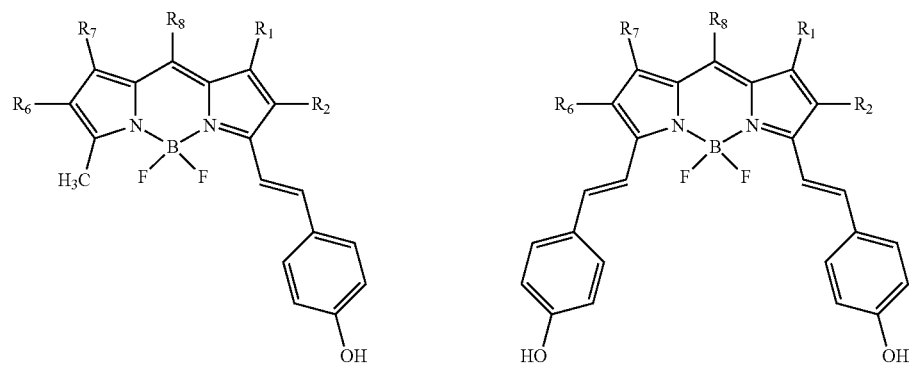

BODIPY intermediate XVIII wherein $R^3=R^5=CH_3$ is prepared first from pyrrole XVII and aldehyde IV, and then in a Knoevenagel reaction one or two methyl substituents are converted to styryl groups in the condensation with p-hydroxybenzaldehyde in the presence of piperidine according to described procedures (M. Baruah, W. Qin, C. Hors, J. Hofkens, R. A. L. Vallée, D. Beljonne, M. Van der Auweraer, W. M. De Broggraeve, N. Boens, *J. Phys. Chem A.*, 2006, 110, 5998-6009; W. Qin, M. Baruah, W. M. De Borggraeve and N. Boens, *J. Photochem. Photobiol., A*, 2006, 183, 190-197).

Intermediates III, IV, VI, XI, XII, XVI and XVII are all known in the art and/or are commercially available.

EXAMPLES

Intermediates

TABLE 1

Structures of Intermediates 1-30

| | |
|---|---|
| 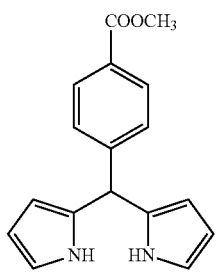 [SMILES: COC(=O)c1ccc(C(c2ccc[nH]2)c2ccc[nH]2)cc1] | Intermediate 1 |
| 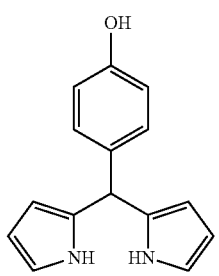 [SMILES: Oc1ccc(C(c2ccc[nH]2)c2ccc[nH]2)cc1] | Intermediate 2 |
| 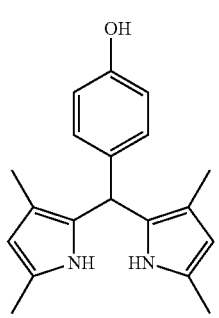 [SMILES: Cc1cc(C)c(C(c2ccc(O)cc2)c2[nH]c(C)cc2C)[nH]1] | Intermediate 3 |

TABLE 1-continued

Structures of Intermediates 1-30

| | |
|---|---|
| 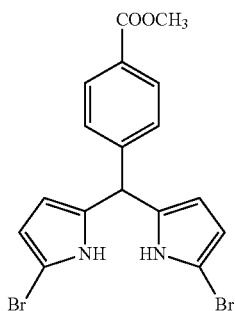 | Intermediate 4 |
| 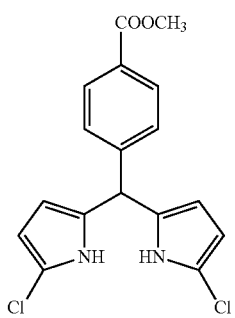 [SMILES: COC(=O)c1ccc(C(c2ccc(Cl)[nH]2)c2ccc(Cl)[nH]2)cc1] | Intermediate 5 |
| 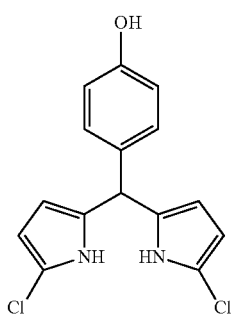 [SMILES: Oc1ccc(C(c2ccc(Cl)[nH]2)c2ccc(Cl)[nH]2)cc1] | Intermediate 6 |
| 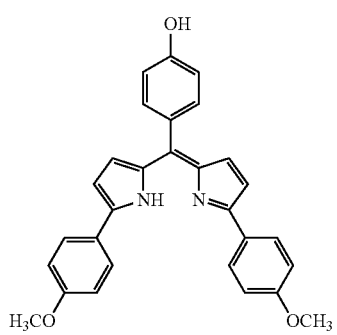 [SMILES: COc1ccc(C2=N/C(=C(/c3ccc(O)cc3)c3ccc(-c4ccc(OC)cc4)[nH]3)C=C2)cc1] | Intermediate 7 |

TABLE 1-continued
Structures of Intermediates 1-30
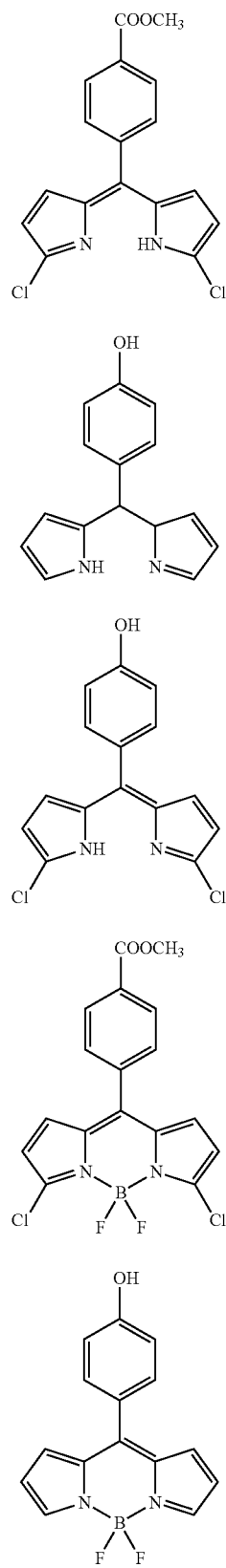
Intermediate 8
Intermediate 9
Intermediate 10
Intermediate 11
Intermediate 12
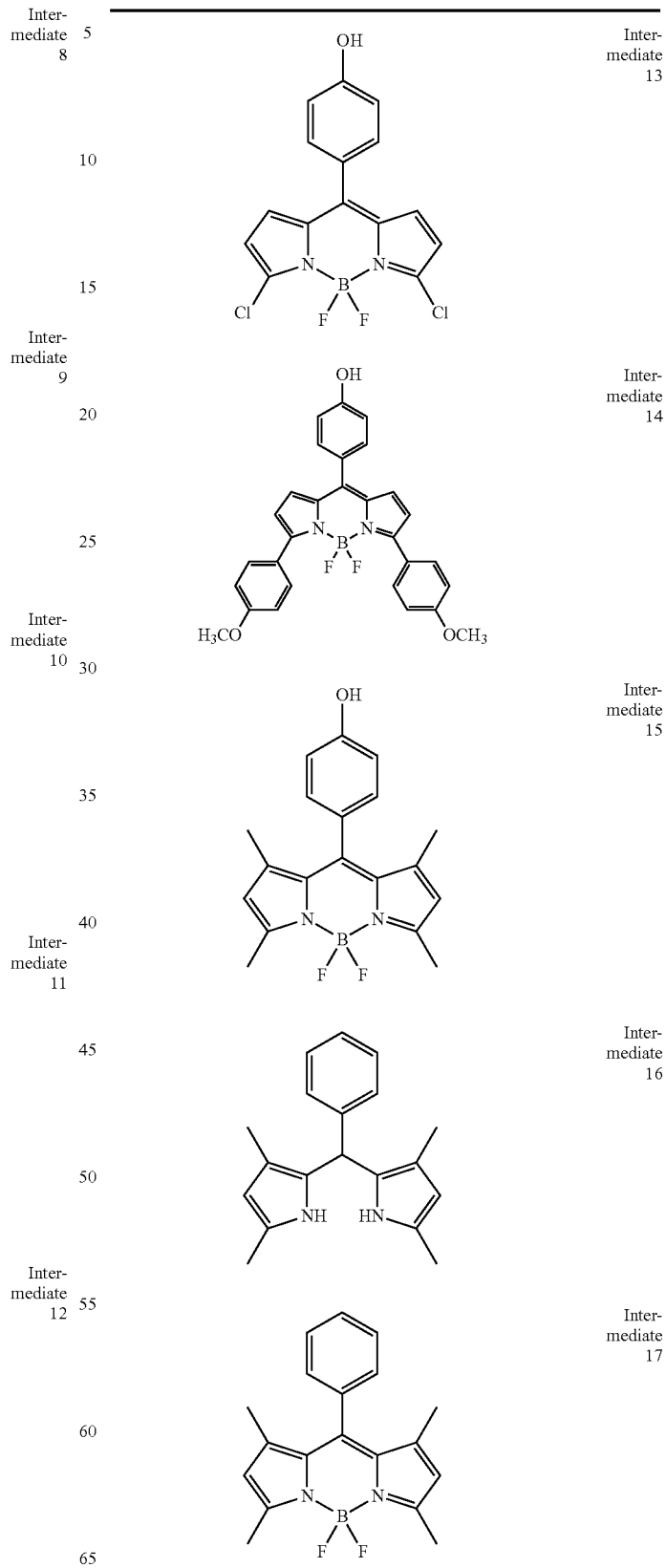
Intermediate 13
Intermediate 14
Intermediate 15
Intermediate 16
Intermediate 17

TABLE 1-continued
Structures of Intermediates 1-30
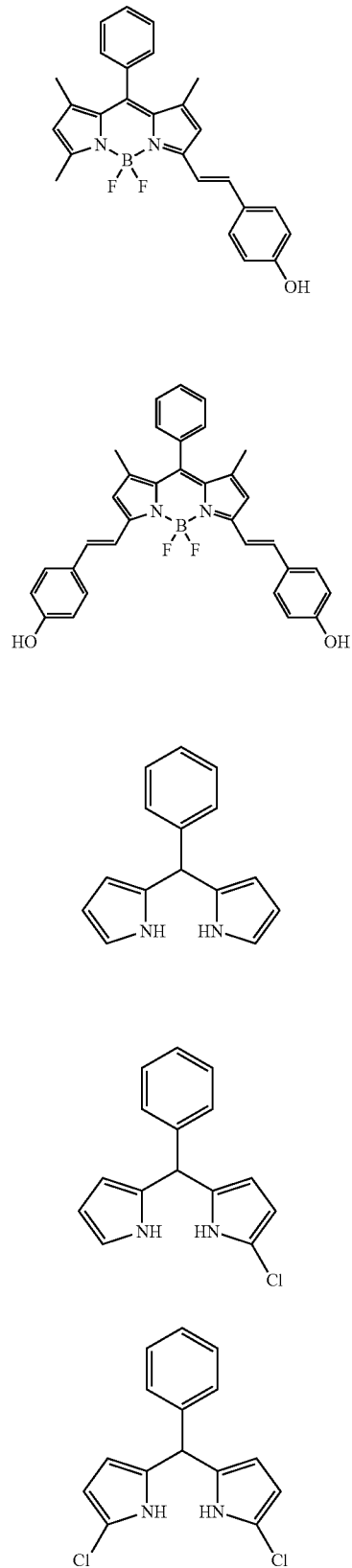
Intermediate 18
Intermediate 19
Intermediate 20
Intermediate 21
Intermediate 22
TABLE 1-continued
Structures of Intermediates 1-30
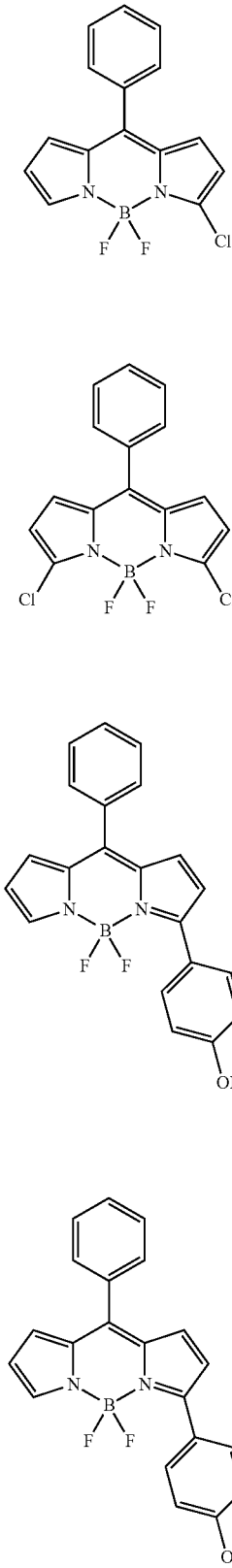
Intermediate 23
Intermediate 24
Intermediate 25
Intermediate 26

TABLE 1-continued

Structures of Intermediates 1-30

| | |
|---|---|
| Intermediate 27 | 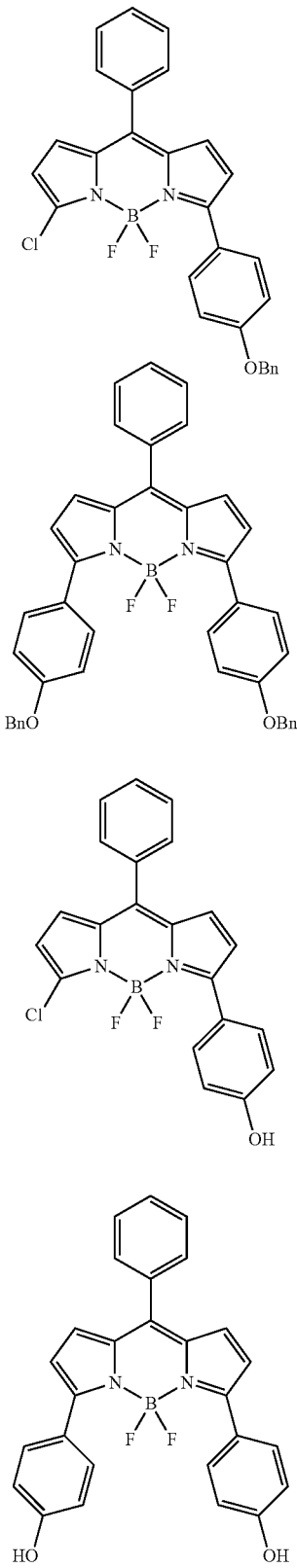 |
| Intermediate 28 | |
| Intermediate 29 | |
| Intermediate 30 | |

Preparation of 5-(4-Methoxycarbonylphenyl)Dipyrromethane, (Intermediate 1)

p-Methoxycarbonylbenzaldehyde (500 mg, 3.05 mmol) was dissolved in pyrrole (5 mL, 77 mmol), and the solution was degassed. TFA (100 µL) was added and the reaction mixture was stirred for 10 min at rt. The reaction was quenched by addition of aqueous sodium hydroxide solution (1 M) following by extraction with ethyl acetate. The organic extracts were washed with water and dried over magnesium sulphate. The solvent and excess pyrrole was removed by vacuum distillation, the residue dissolved in $CH_2Cl_2$ and chromatographed on a column filled with silica using $CH_2Cl_2$/EtOAc as eluent. The title compound (770 mg, 90%) was obtained in a form of yellowish crystals.

Preparation of 5-(4-Hydroxycarbonylphenyl)Dipyrromethane (Intermediate 2)

According to above procedure for the preparation of Intermediate 1, starting from 4-hydroxybenzaldehyde (1.0 g, 8.4 mmol) and pyrrole (14 mL, 215 mmol), the title compound was obtained (1.93 g, 96%). $^1$H NMR ($CDCl_3$, 300 MHz) δ 7.90 (br s, 2H), 7.08 (d, 2H, J=8.6 Hz), 6.77 (d, 2H, J=8.6 Hz), 6.89 (dd, 2H, J=2.7 Hz, J=2.3 Hz), 6.15 (dd, 2H, J=2.7 Hz, J=3.1 Hz), 5.91 (br s, 2H), 5.42 (s, 1H), 4.67 (br s, 1H).

Preparation of 2,4,6,8-Tetramethyl-5-(4-hydroxycarbonylphenyl)Dipyrromethane (Intermediate 3)

4-Hydroxybenzaldehyde (1.22 g, 10 mmol) was dissolved in dry dichloromethane (40 mL). To the solution 2,4-dimethylpyrrole (2.30 g, 20.72 mmol) was added. The solution was purged with $N_2$ and TFA (100 µL) was added. The reaction mixture was stirred at room rt for 2 h. The reaction was quenched by addition of aqueous sodium hydroxide solution (1 M) following by extraction with EtOAc. The organic extracts were washed with water and dried over magnesium sulphate. The aqueous layer was neutralized, and extraction with EtOAc was conducted. The extracts were dried on magnesium sulphate and the solvent was removed by vacuum distillation. The residue was chromatographed on a column filled with silica using $CH_2Cl_2$ and EtOAc as eluent to afford the pure title product (600 mg, 20%). $^1$H NMR ($CDCl_3$, 300 MHz) δ 7.20 (br s, 2H), 7.00 (d, 2H, J=8.4 Hz), 6.76 (d, 2H, J=8.4 Hz), 5.69 (d, 2H, J=2.1 Hz), 5.36 (s, 1H), 2.14 (s, 6H), 1.81 (s, 6H).

Preparation of 1,1'-Dibromo-5-(4-methoxycarbonylphenyl) Dipyrromethane (Intermediate 4)

Dipyrromethane (Intermediate 1, 639 mg, 2.28 mmol) was dissolved in dry THF (40 mL), the solution was purged with argon and cooled to −78° C. To the cooled solution, a THF solution (10 mL) of N-bromosuccinimide (812 mg, 4.56 mmol) was added. The reaction mixture was stirred at −78° C. for 2 h and placed over night to a fridge at −20° C. To the cold reaction mixture, water was added and the reaction mixture was extracted with $CH_2Cl_2$. The extracts were dried over anhydrous magnesium sulphate, the solvent was removed and the residue chromatographed on a column of silica gel using $CH_2Cl_2$ as eluent. To the $CH_2Cl_2$ solutions, tributylamine was added prior to the solvent removal. The title product 500 mg (~50%) was obtained in the form of yellow crystals. Yellow crystals mp 152-154° C.; $^1$H NMR ($CDCl_3$, 300 MHz) δ 8.10 (br s, 2H, NH), 7.99 (d, 2H, J=8.8 Hz), 7.26 (d, 2H, J=8.8 Hz), 6.09 (m, 2H), 5.82 (m, 2H), 5.40 (s, 1H), 3.93 (s, 1H); $^{13}$C NMR ($CDCl_3$, 75 MHz)

δ 167.19 (s), 146.28 (s), 132.72 (s), 130.48 (d), 129.65 (s), 128.73 (d), 111.10 (d), 110.09 (d), 98.24 (s), 52.61 (q), 44.46 (d); MS (CI) m/z 441 (M$^+$+1, 60), 440 (M$^+$+1, 40), 439 (M$^+$+1, 100), 438 (M$^+$+1, 50), 437 (M$^+$+1, 55), 361 (50), 359 (50), 294 (100), 292 (100).

Preparation of 1,1'-Dichloro-5-(4-methoxycarbonylphenyl) Dipyrromethane (Intermediate 5)

According to above procedure for the preparation of Intermediate 4, starting from dipyrromethane (Intermediate 1, 321 mg, 1.35 mmol) and N-chlorosuccinimide (364 mg, 2.70 mmol), the title compound was obtained (260 mg, 55%). Reddish crystals mp (decomposition) 130-131° C.; $^1$H NMR (CDCl$_3$, 300 MHz) δ 8.04 (br s, 2H, NH), 7.95 (d, 2H, J=8.4 Hz), 7.26 (d, 2H, J=8.4 Hz), 5.98 (dd (t), 2H, J=2.9 Hz), 5.82 (dd (t), 2H, J=2.9 Hz), 5.37 (s, 1H), 3.92 (s, 3H); $^{13}$C NMR (CDCl$_3$, 75 MHz) δ 167.36 (s), 146.38 (s), 130.67 (s), 130.47 (d), 129.51 (s), 128.73 (d), 114.52 (s), 109.25 (d), 106.94 (d), 52.69 (q), 44.43 (d); MS (CI) m/z 351 (M$^+$+1, 60), 350 (M$^+$+1, 40), 349 (M$^+$+1, 80), 348 (M$^+$+1, 30), 250 (40), 249 (20), 248 (100).

Preparation of 1,1'-Dichloro-5-(4-hydroxyphenyl)Dipyrromethane (Intermediate 6)

According to above procedure for the preparation of Intermediate 4, starting from dipyrromethane (Intermediate 2, 378 mg, 2.12 mmol) and N-chlorosuccinimide (563 mg, 2.70 mmol), the title compound was obtained 350 mg (54%). Yellow crystals, mp could not be determined ~130° C. crystal change to something of mp>300° C.; $^1$H NMR (CDCl$_3$, 300 MHz) δ 7.87 (br s, 2H, NH), 7.07 (d, 2H, J=8.8 Hz), 6.81 (d, 2H, J=8.8 Hz), 5.97 (dd, 2H, J=2.9 Hz, J=3.7 Hz), 5.83 (dd, 2H, J=2.9 Hz, J=2.9 Hz), 5.34 (br s, 1H, OH), 5.26 (s, 1H); $^{13}$C NMR (CDCl$_3$, 75 MHz) δ 155.32 (s), 133.20 (s), 131.89 (s), 129.94 (d), 116.06 (d), 113.94 (s), 108.75 (d), 106.79 (d), 43.65 (d); MS (CI) m/z 306 (M$^+$+1, 10), 307 (M$^+$+1, 1), 308 (M$^+$+1, 6), 309 (M$^+$+1, 1), 310 (M$^+$+1, 1), 247 (100), 208 (90); MS (EI 70 eV) m/z 306 (M$^+$, 30), 307 (M$^+$, 5), 308 (M$^+$, 15), 206 (100), 207 (15), 208 (25), 170 (80).

Preparation of 1,9-Bis(4-methoxyphenyl)-5-(4-hydroxyphenyl)Dipyrrin (Intermediate 7)

In a dried CH$_2$Cl$_2$ (30 mL), 4-hydroxybenzaldehyde (18 mg) and 2-(4-methoxyphenyl)pyrrole (50 mg) were added. The solution was purged with argon and a drop of TFA was added. The reaction mixture was stirred for 4 h under argon followed by the addition of chloranil (37 mg) in CH$_2$Cl$_2$ (5 mL). The stirring was continued for 2 h, the solvent was evaporated and the residue chromatographed on a column with silica gel using CH$_2$CL$_2$/EtOAc (15%) as eluent to afford 30 mg (45%) of the title product. Blue crystals mp>300° C.; $^1$H NMR (CDCl$_3$, 300 MHz) δ 7.86 (d, 4H, J=8.8 Hz), 7.43 (d, 2H, J=8.8 Hz), 7.03 (d, 4H, J=8.8 Hz), 6.93 (d, 2H, J=8.8 Hz), 6.79 (d, 2H, J=4.4 Hz), 6.74 (d, 2H, J=4.4 Hz), 3.90 (s, 6H, OCH$_3$), OH is not seen; $^{13}$C NMR (CDCl$_3$, 75 MHz) δ 171.67 (s), 160.63 (s), 153.62 (s), 141.74 (s), 133.10 (d), 130.08 (d), 129.30 (d), 127.94 (d), 126.41 (s), 126.18 (s), 115.18 (d), 114.86 (d), 114.63 (d), 55.84 (q); MS (EI, 70 eV) m/z, 448 (M$^+$, 100), 449 (M$^+$, 30), 450 (M$^+$, 5), 433 (10), 341 (10), 278b (30), 173 (75), 158 (60).

Preparation of 1,9-Dichloro-5-(4-methoxycarbonylphenyl) Dipyrrin (Intermediate 8)

According to above procedure for the preparation of Intermediate 7, starting from Intermediate 5 (200 mg, 0.57 mmol) and DDQ (142 mg, 0.63 mmol), the title compound was obtained 170 mg (86%). Orange crystals mp 155-157° C.; $^1$H NMR (CDCl$_3$, 300 MHz) 12.5 (br s, 1H, NH), 8.13 (d, 2H, J=8.4 Hz), 7.54 (d, 2H, J=8.4 Hz), 6.47 (d, 2H, J=4.4 Hz), 6.27 (d, 2H, J=4.4 Hz), 3.98 (s, 3H); $^{13}$C NMR (CDCl$_3$, 75 MHz) δ 166.90 (s), 142.68 (s), 140.40 (s), 138.66 (s), 138.62 (s), 131.35 (s), 131.17 (s), 130.15 (d), 129.46 (d), 117.72 (d), 52.79 (q).

Preparation of 5-(4-Hydroxyphenyl)Dipyrrin (Intermediate 9)

According to above procedure for the preparation of Intermediate 7, starting from Intermediate 2 (700 mg, 3.0 mmol) and DDQ (680 mg, 3.0 mmol), the title compound was obtained 440 mg (63%). Brown crystals mp>300° C.; $^1$H NMR (CDCl$_3$, 300 MHz) δ 7.64 (m, 2H), 7.39 (d, 2H, J=8.4 Hz), 6.85 (d, 2H, J=8.4 Hz), 6.71 (d, 2H, J=4.7 Hz), 6.46 (dd, 2H, J=4.7, J=1.5 Hz), ~5.00 (br s, 1H, OH), NH not seen; $^1$H NMR (D$_6$-DMSO, 300 MHz) δ 7.77 (m, 2H), 7.34 (d, 2H, J=8.8 Hz), 6.89 (d, 2H, J=8.8 Hz), 6.70 (m, 2H), 6.51 (m, 2H), 3.50 (OH associated with DMSO and H$_2$O), NH not seen; $^{13}$C NMR (D$_6$-DMSO, 75 MHz) δ (one singlet is not seen) 144.92 (s), 142.96 (s), 138.75 (d), 134.70 (d), 129.37 (d), 127.67 (s), 117.95 (d), 116.68 (d); MS (EI, 70 eV) m/z 236 (M$^+$, 100), 237 (M$^+$, 100), 219 (20).

Preparation of 1,9-Dichloro-5-(4-hydroxyphenyl)Dipyrrin (Intermediate 10)

According to above procedure for the preparation of Intermediate 7, starting from Intermediate 6 (181 mg, 0.59 mmol) and DDQ (136 mg, 0.60 mmol), the title compound was obtained 150 mg (83%). Brown crystals, mp could not be determined ~120-130° C. crystal change to something of mp>300° C.; $^1$H NMR (CDCl$_3$, 300 MHz) δ~8.00 (br s, 2H, NH, OH), 7.34 (d, 2H, J=8.8 Hz), 6.91 (d, 2H, J=8.8 Hz), 6.59 (d, 2H J=4.4 Hz), 6.28 (d, 2H, J=4.4 Hz); $^{13}$C NMR (CDCl$_3$, 75 MHz) δ 169.99 (s), 157.35 (s), 141.83 (s), 141.21 (s), 133.10 (d), 130.50 (d), 128.35 (s), 117.17 (d), 115.28 (d); MS (EI, 70 eV) m/z 304 (M$^+$, 10), 305 (M$^+$, 5), 306 (M$^+$, 5), 269 (30), 250 (50), 248 (100), 246 (90).

Preparation of 4,4-Difluoro-8-(4-methoxycarbonylphenyl)-3,5-dichloro-4-bora-3a,4a-diaza-s-indacene (Intermediate 11)

Dichloromethane solution of Intermediate 8 (220 mg, 0.63 mmol) was purged with argon. To the solution was added triethylamine (550 μL, 7.6 mmol) and the solution was stirred for 0.5 h at rt. BF$_3$-etherate (4.0 mL, 7.6 mmol) was added and the reaction was stirred for one h. The reaction was quenched by addition of 1M aqueous solution of sodium hydroxide. The layers were separated and the aqueous layer was extracted with CH$_2$Cl$_2$. The organic extracts were dried over magnesium sulphate, the solvent was removed and the residue was chromatographed on silica gel using CH$_2$Cl$_2$ or CH$_2$CL$_2$/EtOAc as eluent to afford the title product (140 mg, 55%). Deep red crystals mp 219-220° C., crystallized three times from chloroform/cyclohexane mixture; $^1$H NMR (CDCl$_3$, 300 MHz) δ 8.20 (d, 2H, J=8.4 Hz), 7.58 (d, 2H, J=8.4 Hz), 6.81 (d, 2H, J=4.4 Hz), 6.47 (d, 2H, J=4.4 Hz), 4.00 (s, 3H); $^{13}$C NMR (CDCl$_3$, 75 MHz) δ 166.48 (s), 146.13 (s), 142.68 (s), 136.97 (s), 133.93 (s), 132.74 (s), 131.81 (s), 130.80 (d), 130.10 (d), 119.70 (d), 52.99 (q); MS (EI, 70 eV) m/z 394 (M$^+$, 100), 395 (M$^+$, 30), 396 (M$^+$, 60), 375 (5), 359 (10), 335 (30), 336 (5), 337 (20).

Preparation of 4,4-Difluoro-8-(4-hydroxyphenyl)-4-bora-3a,4a-diaza-s-indacene (Intermediate 12)

Toluene solution of one equivalent of dipyrrin (Intermediate 9, 440 mg, 1.86 mmol) was purged with argon. To the solution was added triethylamine (2.6 mL, 18.6 mmol) and the solution was heated at 70° C. for 0.5 hour. Then, the BF$_3$ etherate (3.2 g, 7.1 mL, 22.3 mmol) was added and the reaction was heated at the temperature of reflux for two hours. To the cooled reaction mixture, an aqueous solution of sodium hydroxide (1 M) was added. The layers were separated and the aqueous layer was brought to pH ~5-6 by addition of HCl. The aqueous layer was extracted with CH$_2$Cl$_2$ and EtOAc, dried over magnesium sulphate and the solvent was removed by distillation. The residue was chromatographed on silica using CH$_2$CL$_2$/EtOAc as eluent to afford the title product 340 mg (64%). Orange crystals mp 153° C.; crystallized three times from chloroform/cyclohexane mixture; $^1$H NMR (CDCl$_3$, 300 MHz) δ 7.93 (m, 2H), 7.47 (d, 2H, J=8.8 Hz), 6.99 (m, 2H), 6.97 (d, 2H, J=8.8 Hz), 6.56 (m, 2H), 6.15 (broad s, 1H, OH); $^{13}$C NMR (CDCl$_3$, 75 MHz) δ 159.13 (s), 147.90 (s), 143.79 (d), 135.20 (s), 133.03 (d), 131.85 (d), 126.57 (s), 118.79 (d), 116.02 (d); MS (EI, 70 eV) m/z 283 (M$^+$, 80), 284 (M$^+$, 100), 285 (M$^+$, 20), 263 (20), 198 (30), 155 (50), 121 (40), 91 (100).

Preparation of 4,4-Difluoro-8-(4-hydroxyphenyl)-3,5-dichloro-4-bora-3a,4a-diaza-s-indacene (Intermediate 13)

According to the procedure for intermediate 12, the reaction of Intermediate 10 (220 mg, 0.72 mmol) furnished 120 mg (47%) of the title product. Red crystals mp 224° C.; crystallized three times from chloroform/cyclohexane mixture; $^1$H NMR (CDCl$_3$, 300 MHz) δ 7.42 (d, 2H, J=8.8 Hz), 6.99 (d, 2H, J=8.8 Hz), 6.89 (d, 2H J=4.4 Hz), 6.45 (d, 2H, J=4.4 Hz), 5.80 (br s, 1H, OH); $^{13}$C NMR (CDCl$_3$, 75 MHz) δ 172.72 (s), 159.64 (s), 144.31 (s), 134.00 (s), 132.94 (d), 132.02 (d), 127.74 (s), 119.03 (d), 116.25 (d); MS (EI, 70 eV) m/z 352 (M$^+$, 15), 353 (M$^+$, 5), 354 (M$^+$, 5), 317 (15), 304 (15), 269 (40), 232 (40), 198 (35), 155 (60), 121 (40), 91 (100).

Preparation of 4,4-Difluoro-8-(4-hydroxyphenyl)-3,5-bis(4-methoxyphenyl)-4-bora-3a,4a-diaza-s-indacene (Intermediate 14)

According to the procedure for Intermediate 12, the reaction of Intermediate 7 (60 mg, 0.13 mmol) furnished 20 mg (30%) of the title product. Deep blue crystals mp 250° C.; recrystalyzed three times from chloroform/cyclohexane mixture; $^1$H NMR (CDCl$_3$, 300 MHz) δ 7.88 (d, 4H, J=8.8 Hz), 7.49 (d, 2H, J=8.8 Hz), 6.99 (d, 2H, J=8.8 Hz), 6.97 (d, 4H, J=8.8 Hz), 6.89 (d, 2H, J=4.4 Hz), 6.62 (d, 2H, J=4.4 Hz), 3.86 (s, 6H, OCH$_3$), OH is not seen; $^{13}$C NMR (CDCl$_3$, 75 MHz) δ 161.04 (s), 157.88 (s), 151.90 (s), 132.82 (d), 131.55 (s), 131.49 (s), 131.43 (d), 130.73 (d), 127.53 (s), 125.69 (s), 120.72 (d), 115.68 (d), 114.19 (d), 55.69 (q); MS (EI, 70 eV) m/z 495 (M$^+$, 20), 496 (M$^+$, 100), 497 (M$^+$, 30), 480 (5), 481 (35), 482 (7), 206 (50), 170 (40).

Preparation of 4,4-Difluoro-8-(4-hydroxyphenyl)-1,3,5,7-tetramethyl-4-bora-3a,4a-diaza-s-indacene (Intermediate 15)

Intermediate 3 (800 mg, 2.72 mmol) and DDQ (680 mg, 3.0 mmol) were suspended in dry toluene (50 mL). The suspension was heated at reflux 1 h. To the cooled reaction mixture triethylamine was added (4 mL, 28.7 mmol), followed by BF$_3$ etherate (6 mL, 20.5 mmol). The reaction mixture was heated at 70° C. over night. To the cooled reaction mixture aqueous solution of NaOH (1M, 30 mL) was added and the layers were separated. The aqueous layer was neutralized with 4 M HCl, and extraction with EtOAc was carried out. The combined organic layers were dried over MgSO$_4$ and the solvent was removed. The residue was chromatographed on column of silica gel using CH$_2$Cl$_2$/EtOAc as eluent to afford the pure title product (350 mg, 37%). $^1$H NMR (CDCl$_3$, 300 MHz) δ 7.12 (d, 2H, J=8.4 Hz), 6.94 (d, 2H, J=8.4 Hz), 5.97 (s, 2H), 5.18 (br s, 1H), 2.54 (s, 6H), 2.14 (s, 6H).

Preparation of 2,4,6,8-Tetramethyl-5-phenyldipyrromethane (Intermediate 16)

According to above procedure for the preparation of Intermediate 3, starting from benzaldehyde (0.89 g, 8.39 mmol) and 2,4-dimethylpyrrole (2.73 g, 21.0 mmol), the title compound was obtained (1.20 g, 52%). $^1$H NMR (CDCl$_3$, 300 MHz) δ/ppm: 7.34-7.14 (m, 7H), 5.70 (d, J=2.4 Hz, 2H), 5.44 (s, 1H), 2.15 (s, 6H), 1.82 (s, 6H).

Preparation of 4,4-Difluoro-8-phenyl-1,3,5,7-tetramethyl-4-bora-3a,4a-diaza-s-indacene (Intermediate 17)

According to above procedure for the preparation of Intermediate 15, starting from Intermediate 16 (1.37 g, 4.9 mmol) and DDQ (1.11 g, 4.9 mmol) in the first step, and triethylamine (3.5 mL, 25 mmol), and BF$_3$ etherate (7 mL, 25 mmol) in the second step, the title compound was obtained (330 mg, 21%). $^1$H NMR (CDCl$_3$, 600 MHz) δ/ppm: 7.50-7.46 (m, 3H), 7.29-7.27 (m, 2H), 5.98 (s, 2H), 2.56 (s, 6H), 1.37 (s, 6H); $^{13}$C NMR δ/ppm: 155.6 (s), 143.3 (s), 141.9 (s), 135.1 (s), 131.6 (s), 129.3 (d), 129.1 (d), 128.1 (d), 121.3 (d), 14.7 (q), 14.5 (q).

Preparation of 4,4-Difluoro-8-phenyl-1,5,7-trimethyl-3-[2-(4-hydroxyphenyl)ethenyl)]-4-bora-3a,4a-diaza-s-indacene (Intermediate 18) and 4,4-Difluoro-8-phenyl-1,7-dimethyl-3,5-bis[2-(4-hydroxyphenypetheny)ethanyl)]-4-bora-3a,4a-diaza-s-indacene (Intermediate 19)

Intermediate 17 (200 mg, 0.62 mmol), 4-hydroxybenzaldehyde (0.188 g 1.24 mmol), piperidine (0.4 mL, 4.0 mmol), acetic acid (0.5 mL, 8.7 mmol) and anhydrous toluene (2 mL) were mixed in a test tube for microwave reactions and the test tube was sealed. The mixture was heated in a microwave reactor 30 min at 190° C. at the power of 200 W. To the reaction mixture water was added (20 mL) and extraction with EtOAc (3×50 mL) was carried out. The extracts were dried over anhydrous Na$_2$SO$_4$, filtered and the solvent was evaporated. The residue was chromatographed on a column of silica gel using 5 CH$_2$Cl$_2$/MeOH (5%) as eluent to afford title compound 18 (90 mg, 34%), and title compound 19 (35 mg, 11%).

Intermediate 18: $^1$H NMR (CDCl$_3$, 300 MHz) δ/ppm: 7.54 (d, J=16.1 Hz, 1H), 7.52-7.48 (m, 5H), 7.32-7.29 (m, 2H), 7.18 (d, J=16.1 Hz, 1H), 6.84 (d, J=8.8 Hz, 2H), 6.58 (s, 1H), 5.99 (s, 1H), 4.94 (s, 1H), 2.59 (s, 3H), 1.43 (s, 3H), 1.39 (s, 3H).

Intermediate 19: $^1$H NMR (CDCl$_3$, 300 MHz) δ/ppm: 7.57 (d, J=16.6 Hz, 2H), 7.53-7.45 (m, 7H), 7.34-7.29 (m, 2H), 7.19 (d, J=16.6 Hz, 2H), 6.89 (d, J=8.1 Hz, 4H), 6.59 (s, 2H), 1.42 (s, 6H).

Preparation of 5-Phenyldipyrromethane (Intermediate 20)

According to above procedure for the preparation of Intermediate 1, starting from benzaldehyde (4.00 g, 17.9 mmol) and pyrrole (63.22 g, 215 mmol), the title compound was obtained (6.67 g, 81%). $^1$H NMR (CDCl$_3$, 300 MHz) δ/ppm: 7.89 (br s, 2H), 7.35-7.18 (m, 5H), 6.68 (dd, J=4.1, 2.6 Hz, 2H), 6.15 (dd, J=5.8, 2.8 Hz, 2H), 5.94-5.88 (m, 2H), 5.46 (s, 1H); $^{13}$C NMR (CDCl$_3$, 75 MHz) δ/ppm: 142.2 (s), 132.6 (s), 128.8 (d), 128.6 (d), 127.1 (d), 117.3 (d), 108.6 (d), 107.4 (d), 44.1 (d).

Preparation of 1-Chloro-5-phenyldipyrromethane (Intermediate 21) and 1,1'-Dichloro-5-phenyldipyrromethane (Intermediate 22)

According to above procedure for the preparation of Intermediate 4, starting from dipyrromethane (Intermediate 20, 3.68 g, 16.5 mmol) and N-chlorosuccinimide (4.86 g, 21.4 mmol), a mixture of the title compounds, Intermediate 21 (1.21 g, 24%) and Intermediate 22 were obtained (0.56 g, 13%).

Intermediate 21: ¹H NMR (CDCl₃, 600 MHz) δ/ppm: 7.82 (br s, 1H), 7.75 (br s, 1H), 7.31-7.17 (m, 5H), 6.65-6.64 (m, 1H), 6.14 (dd J=5.8, 2.9 Hz, 1H), 5.94-5.93 (m, 1H), 5.90-5.89 (m, 1H), 5.78-5.77 (m, 1H), 5.34 (s, 1H).

Intermediate 22: ¹H NMR (CDCl₃, 600 MHz) δ/ppm: 7.76 (br s, 2H), 7.36-7.19 (m, 5H), 5.97-5.95 (m, 2H), 5.83-5.82 (m, 2H), 5.30 (s, 1H).

Preparation of 4,4-Difluoro-3-chloro-8-phenyl-4-bora-3a,4a-diaza-s-indacene (Intermediate 23) and 4,4-Difluoro-3,5-dichloro-8-phenyl-4-bora-3a,4a-diaza-s-indacene (Intermediate 24)

A mixture of Intermediate 21 and Intermediate 22 (1.14 g, ratio 21/22 1:2) and DDQ (0.94 g, 4.13 mmol) were dissolved in anhydrous CH₂Cl₂ (15 mL). The mixture was stirred at rt 1 h. After the reaction was completed, the mixture was filtered and the filtrate was conocentrated on a rtoational evaporator. To the concentrated solution in CH₂Cl₂ (20 mL), under N₂-inert atmosphere, TEA (3.0 mL, 21 mmol) and BF₃OEt₂ (5.5 mL, 21 mmol) were added and the stirring was continued for 24 h. The next day, a solution of NaOH 2M (25 mL) was added and the layers were separated. The aqueous, layer was accidified to neutral by addition of HCl, and extractions with CH₂Cl₂ (2×50 mL) and ethyl acetate (3×50 mL) were crried out. The cobined organic extracts were dried over anhydrous MgSO₄, filtered and the solvent was removed on a rotational evaporator. The residue was chromatographed on a column of silica gel using ethyl acetate/CH₂Cl₂ (1:4) as an eluentl to afford the title compounds.

Intermediate 23: ¹H NMR (CDCl₃, 600 MHz) δ/ppm: 7.93 (s, 1H), 7.56-7.52 (m, 5H), 6.90 (d, J=4.1 Hz, 1H), 6.88 (d, J=4.1 Hz, 1H), 6.56 (d, J=3.6 Hz, 1H), 6.42 (d, J=4.3 Hz, 1H); ¹³C NMR (CDCl₃, 150 MHz) δ/ppm: 146.0 (s), 144.8 (d), 135.1 (s), 134.3 (s), 133.4 (s), 132.2 (d), 131.8 (d), 131.2 (d), 130.8 (d), 128.8 (d), 119.3 (d), 118.8 (d), 53.75 (s).

Intermediate 24: ¹H NMR (CDCl₃, 300 MHz) δ/ppm: 7.59-7.45 (m, 5H), 6.84 (d, J=4.2 Hz, 2H), 6.43 (d, J=4.2 Hz, 2H); ¹³C NMR (CDCl₃, 75 MHz) δ/ppm: 145.2 (s), 144.3 (s), 134.1 (s), 132.7 (s), 132.0 (d), 131.2 (d), 130.7 (d), 128.9 (d), 119.2 (d).

Preparation of 4,4-Difluoro-3-[4-(benzyloxy)phenyl]-8-phenyl-4-bora-3a,4a-diaza-s-indacene (Intermediate 25)

4,4-Difluoro-3-chloro-8-phenyl-4-bora-3a,4a-diaza-s-indacene (Intermediate 23, 0.300 g, 0.992 mmol) and p-benzylhydroxyphenyl boronic acid (0.452 g, 1.98 mmol) were dissolved in toluene (5 mL). To the mixture, an aqueous solution (3 mL) of Na₂CO₃ (0.315 g, 2.98 mmol) was added. The apparatus was purged with N₂ and Pd(PPh₃)₄ (0.115 g, 0.099 mmol) was added. The reaction mixture was heated at the temperature of reflux under inert atmosphere over night. The layers were separated, and the aqueous layer was extracted with CH₂Cl₂ (4×25 mL). The extracts were dried over Na₂SO₄, filtered and the solvent was removed on a rotational evaporator. The residue was chromatographed on a column of silica gel using hexane/CH₂Cl₂ (1:4) as eluent. The title product was obtained (250 mg, 56%). ¹H NMR (CDCl₃, 600 MHz) δ/ppm: 7.98 (d, J=8.8 Hz, 2H), 7.81 (br s, 1H), 7.58-7.56 (m, 3H), 7.53-7.52 (m, 2H), 7.46 (d, J=7.3 Hz, 2H), 7.41 (dd, J=7.7, 7.3 Hz, 2H), 7.35 (t, J=7.3 Hz, 1H), 7.09 (d, J=8.8 Hz, 2H), 6.96 (d, J=4.5 Hz, 1H), 6.80 (d, J=4.0 Hz, 1H), 6.69 (d, J=4.5 Hz, 1H), 6.50-6.49 (m, 1H), 5.15 (s, 2H).

Preparation of 4,4-Difluoro-3-(4-hydroxyphenyl)-8-phenyl-4-bora-3a,4a-diaza-s-indacene (Intermediate 26)

4,4-Difluoro-3-[4,4-(benzyloxy)phenyl]-8-phenyl-4-bora-3a,4a-diaza-s-indacene (Intermediate 25, 0.24 g, 0.533 mmol) was dissolved in a mixture of dry ethanol and CHCl₃ (35 mL, 7:1), transferred to the hydrogenation vessel and Pd/C (0.5 g) was added. The reaction mixture was hydrogenated at rt under H₂ pressure of 63 psi 24 h. The mixture was filtered through filter paper (blue ribbon) and the solvent was removed on a rotary evaporator. The residue was chromatographed on a column of silica gel using CH₂CL₂/EtOAc (1:4) as eluent. The title product was obtained (34 mg, 18%). ¹H NMR (CDCl₃, 600 MHz) δ/ppm: 7.92 (d, J=8.8 Hz, 2H), 7.81 (br s, 1H), 7.59-7.55 (m, 3H), 7.55-7.51 (m, 2H), 6.90 (d, J=8.8 Hz, 2H), 6.97 (d, J=4.6 Hz, 1H), 6.90 (d, J=8.8 Hz, 2H), 6.80-6.78 (m, 1H), 6.68 (d, J=4.6 Hz, 1H), 6.51-6.49 (m, 1H), 4.91 (br s, 1H).

Preparation of 4,4-Difluoro-3-[4-(benzyloxy)phenyl)]-5-chloro-8-phenyl-4-bora-3a,4a-diaza-s-indacene (Intermediate 27) and 4,4-difluoro-3,5-bis[4-(benzyloxy)phenyl)]-8-phenyl-4-bora-3a,4a-diaza-s-indacene (Intermediate 28)

According to above procedure for the preparation of Intermediate 25, starting from 4,4-difluoro-3,5-dichloro-8-phenyl-4-bora-3a,4a-diaza-s-indacene (Intermediate 24, 250 mg, 0.74 mmol) p-benzylhydroxyphenyl boronic acid (0.338 g, 1.48 mmol) and Pd(PPh₃)₄ (86 mg, 0.074 mmol), a mixture of the title compounds, Intermediate 27 (20 mg, 5%) and Intermediate 28 were obtained (205 mg, 44%).

Intermediate 27: ¹H NMR (CDCl₃, 600 MHz) δ/ppm: 7.98 (d, J=8.9 Hz, 2H), 7.81 (br s, 1H), 7.58-7.51 (m, 5H), 7.47-7.35 (m, 5H), 7.09 (d, J=8.9 Hz, 2H), 6.97 (d, J=4.4 Hz, 1H), 6.81 (d, J=3.9 Hz, 1H), 6.70 (d, J=4.4 Hz, 1H), 6.50 (dd, J=3.9, 1.8 Hz, 1H), 5.15 (s, 2H).

Intermediate 28: ¹H NMR (CDCl₃, 600 MHz) δ/ppm: 7.88 (d, J=8.9 Hz, 4H), 7.58-7.51 (m, 5H), 7.48-7.44 (m, 5H), 7.41-7.38 (m, 5H), 7.03 (d, J=8.9 Hz, 4H), 6.84 (d, J=4.3 Hz, 2H), 6.60 (d, J=4.3 Hz, 2H), 5.11 (s, 4H).

Preparation of 4,4-Difluoro-3-(4-hydroxyphenyl)-5-chloro-8-phenyl-4-bora-3a,4a-diaza-s-indacene (Intermediate 29)

According to above procedure for the preparation of Intermediate 26, starting from 4,4-difluoro-3-[4-(benzyloxy)phenyl)]-5-chloro-8-phenyl-4-bora-3a,4a-diaza-s-indacene (Intermediate 27, 20 mg) and Pd/C, hydrogenation is conducted at rt under atmospheric H₂ pressure (under baloon of H₂) over 3 days. The mixture is filtered through filter paper (blue ribbon) and the solvent is removed on a rotary evaporator. The residue is chromatographed on a column of silica gel using CH₂CL₂/EtOAc as eluent. The title product is obtained.

Preparation of 4,4-Difluoro-3,5-bis(4-hydroxyphenyl)-8-phenyl-4-bora-3a,4a-diaza-s-indacene (Intermediate 30)

According to above procedure for the preparation of Intermediate 26, starting from 4,4-difluoro-3,5-bis[4-(benzyloxy)phenyl)]-8-phenyl-4-bora-3a,4a-diaza-s-indacene (Intermediate 28, 200 mg) and Pd/C (1 g), hydrogenation was conducted at rt under atmospheric H₂ pressure (under baloon of H₂) over 3 days. The mixture was filtered through filter paper (blue ribbon) and the solvent was removed on a rotary evaporator. The residue was chromatographed on a column of silica gel using CH₂Cl₂/EtOAc/CH₃OH (73:20:7) as eluent. The title product was obtained (7 mg, 7%). ¹H NMR (CD₃OD, 300 MHz) δ/ppm: 7.81 (d, 4422)

TABLE 2
Structures of Examples 1-12
Example 1
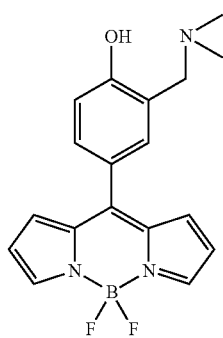
Example 2
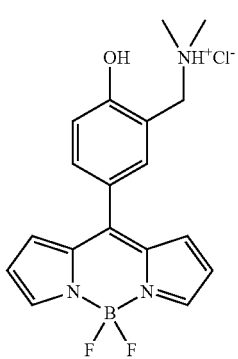
Example 3
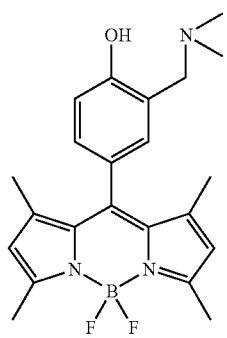
Example 4
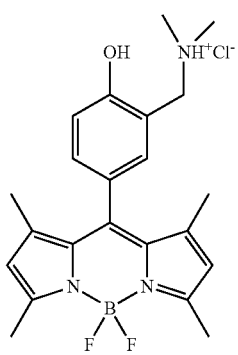
TABLE 2-continued
Structures of Examples 1-12
Example 5
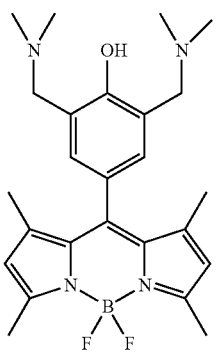
Example 6
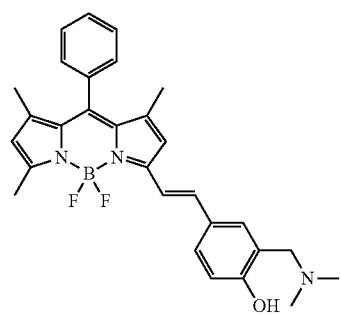
Example 7
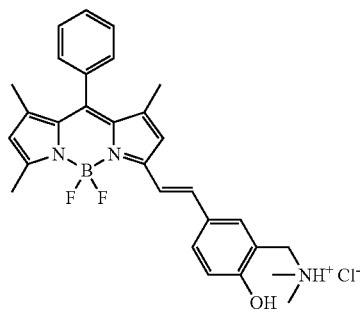
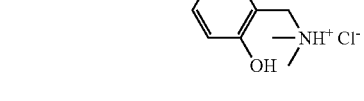
Example 8
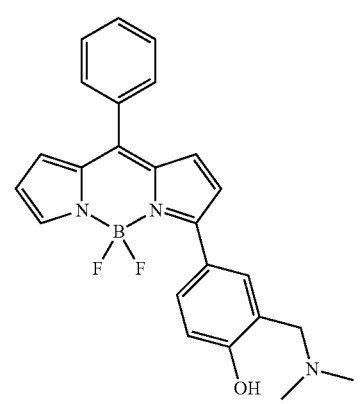

TABLE 2-continued

Structures of Examples 1-12

Example 9

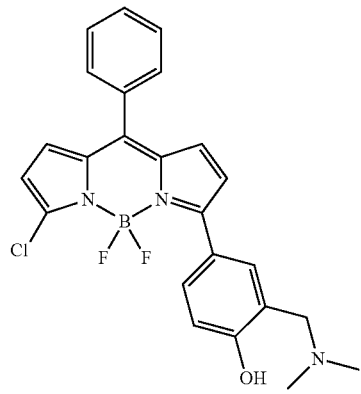

Example 10

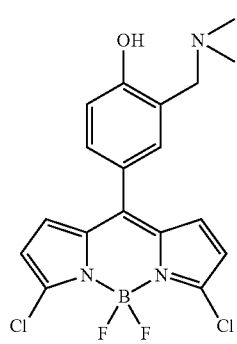

Example 11

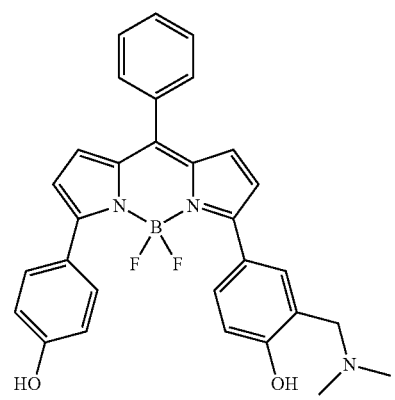

Example 12

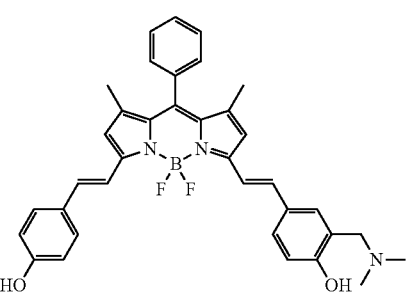

Example 1

Procedure for the Preparation of 4,4-difluoro-8-[3-(N,N-dimethylaminomethyl)-4-hydroxyphenyl]-4-bora-3a,4a-diaza-s-indacene 4,4-difluoro-8-(4-hydroxyphenyl)-4-bora-3a,4a-diaza-s-indacene (Intermediate 12, 500 mg, 1.76 mmol), anhydrous potassium carbonate (365 mg, 2.64 mmol) and Eschenmoser's salt (N,N-dimethylmethyleneiminium chloride, 246 mg, 2.64 mmol) were added to anhydrous toluene (50 mL). The reaction mixture was refluxed over night. The next day the toluene was poured off and filtered through a sinter funnel, and the dark tarry residue washed with EtOAc (3×75 mL). The organic solutions were combined and evaporated yielding crude product which was purified on a column of $Al_2O_3$ (activity IV) using $CH_2Cl_2$-EtOc (0→100%) as eluent. 470 mg (78%) of the crude title product as orange crystals was obtained, which was transformed to the corresponding HCl salt without further purification.

Example 2

Preparation of 4,4-difluoro-8-[3-(N,N-dimethylammoniummethyl)-4-hydroxyphenyl]-4-bora-3a,4a-diaza-s-indacene hydrochloride The amine (Example 1) obtained in the above reaction (470 mg, 1.37 mmol) was dissolved in anhydrous diethyl ether ($Et_2O$, 10 mL) to which $Et_2O$ saturated with HCl was added dropvise until further additions did not result in the additional precipitate. The precipitate was filtered off on a Hirsch sinter funnel (G4), washed with $Et_2O$ and dried in a desiccator over KOH. Orange crystals (230 mg, 35% in two steps); $^1H$ NMR (600 MHz, DMSO-$d_6$) δ/ppm 11.28 (br s, 1H), 9.87 (br s, 1H), 8.09 (br s, 2H), 7.80 (d, 1H, J=2.2 Hz), 7.66 (dd, 1H, J=2.2 Hz, J=8.5 Hz), 7.23 (d, 1H, J=8.5 Hz), 7.18 (d, 2H, J=4.0 Hz), 6.70 (dd, 2H, J=1.8 Hz, J=4.0 Hz), 4.32 (s, 2H), 2.79 (s, 6H).

Example 3

Preparation of 4,4-difluoro-1,3,5,7-tetramethyl-8-[3-(N,N-dimethylaminomethyl)-4-hydroxyphenyl]-4-bora-3a,4a-diaza-s-indacene According to the procedure in Example 1, starting from 4,4-difluoro-1,3,5,7-tetramethyl-8-(4-hydroxyphenyl)-4-bora-3a,4a-diaza-s-indacene (Intermediate 15, 280 mg, 0.85 mmol), 250 mg (74%) of the title product was obtained in the form of orange crystals. $^1H$ NMR (300 MHz, $CDCl_3$) δ/ppm 7.05 (dd, 1H, J=2.0 Hz, J=8.2 Hz), 6.95 (d, 1H, J=8.2 Hz), 6.86 (d, 1H, J=2.0 Hz), 5.96 (s, 2H), 3.69 (s, 2H), 2.54 (s, 6H), 2.36 (s, 6H), 1.45 (s, 6H).

Example 4

Preparation of 4,4-difluoro-1,3,5,7-tetramethyl-8-[3-(N,N-dimethylammoniummethyl)-4-hydroxyphenyl]-4-bora-3a,4a-diaza-s-indacene hydrochloride According to the procedure in Example 2 the amine obtained in the above reaction 4,4-difluoro-1,3,5,7-tetramethyl-8-[3-(N,N-dimethylaminomethyl)-4-hydroxyphenyl]-4-bora-3a,4a-diaza-s-indacene (Example 3, 200 mg, 0.50 mmol) gave 215 mg (99%) of the title product in the form of orange crystals. $^1H$ NMR (300 MHz, DMSO-$d_6$) δ/ppm 10. 81 (br s, 1H), 9.65 (br s, 1H), 7.38 (d, 1H, J=2.1 Hz), 7.28 (dd, 1H, J=2.1 Hz, J=8.3 Hz), 7.15 (d, 1H, J=8.3 Hz), 6.19 (s, 2H), 4.27 (s, 2H), 2.73 (s, 6H), 2.45 (s, 6H), 1.45 (s, 6H).

Example 5

Preparation of 4,4-difluoro-1,3,5,7-tetramethyl-8-[3,5-bis(N,N-dimethylammonium-methyl)-4-hydroxyphenyl]-4-bora-3a,4a-diaza-s-indacene hydrochloride 4,4-difluoro-1,3,5,7-tetramethyl-8-(4-hydroxyphenyl)-4-bora-3a,4a-diaza-s-indacene (Intermediate 15, 100 mg, 0.29 mmol), was mixed with 40% aqueous solution of dimethylamine (8.2 mL, 100 equivalents), and 37% formaline (4.2 mL, 100 equivalents) and the mixture was refluxed 2 h. After cooling to room temperature, solid NaCl (10 equivalents) was added, and the most of $H_2O$ was evaporated. The residue was extracted with EtOAc (3×50 mL). Organic extracts were dried over anhydrous $MgSO_4$, filtered and the solvent was removed on a rotary evaporator. The residue was chromatographed on a column of $Al_2O_3$ (activity IV) using $CH_2Cl_2$-EtOAc (0→100%) as eluent. 30 mg (22%) of the crude title product as orange crystals was obtained. $^1H$ NMR ($CDCl_3$, 300 MHz) δ/ppm: 8.08 (s, 2H), 6.08 (s, 2H), 3.78 (s, 4H), 2.91 (s, 6H), 2.23 (s, 12H), 1.46 (s, 6H).

Example 6

Preparation of 4,4-difluoro-1,5,7-trimethyl-3-{2-[3-(N,N-dimethylaminomethyl)-4-hydroxyphenyl]ethenyl}-8-phenyl-4-bora-3a,4a-diaza-s-indacene According to the procedure in Example 1, starting from 4,4-Difluoro-8-phenyl-1,5,7-trimethyl-3-[2-(4-hydroxyphenyl)ethenyl)]-4-bora-3a,4a-diaza-s-indacene (Intermediate 18, 84 mg, 0.194 mmol), Eschenmoser salt (23 mg, 0.255 mmol) and $K_2CO_3$ (35 mg, 0.255 mmol) the title product was obtained after chromatography in the form of red crystals (29 mg, 20%).
$^1H$ NMR ($CDCl_3$, 600 MHz) δ/ppm: 7.51-7.47 (m, 4H), 7.36-7.34 (m, 1H), 7.31-7.30 (m, 3H), 7.17 (d, J=16.1 Hz, 1H), 6.81 (d, J=8.3 Hz, 1H), 6.57 (s, 1H), 5.99 (s, 1H), 3.70 (s, 2H), 2.60 (s, 3H), 2.36 (s, 6H), 1.42 (s, 3H), 1.38 (s, 3H); $^{13}C$ NMR ($CDCl_3$, 150 MHz) δ/ppm: 159.9 (s), 154.3 (s), 154.0 (s), 142.9 (s), 142.1 (s), 139.9 (s), 136.9 (d), 135.4 (s), 133.0 (s), 131.7 (s), 129.5 (d), 129.2 (d), 129.0 (d), 128.4 (d), 127.9 (s), 127.2 (d), 122.5 (s), 121.1 (d), 117.7 (d), 116.6 (d), 116.2 (d), 62.8 (t), 44.6 (q), 14.8 (q), 14.4 (q), 14.3 (q).

Example 7

Preparation of 4,4-difluoro-1,5,7-trimethyl-343-(N,N-dimethylammoniummethyl)-4-hydroxyphenyl)-8-phenyl-4-bora-3a,4a-diaza-s-indacene hydrochloride According to the procedure in Example 2 the amine obtained in the above reaction 4,4-difluoro-1,5,7-trimethyl-3-[(N,N-dimethylaminomethyl)-4-hydroxyphenyl]-8-phenyl-4-bora-3a,4a-diaza-s-indacene (Example 6, 10 mg, 0.021 mmol) gave 11 mg (99%) of the title product in the form of violet crystals.
$^1H$ NMR ($CD_3OD$, 600 MHz) δ/ppm: 7.58-7.57 (m, 1H), 7.50-7.47 (m, 4H), 7.45 (d, J=16.1 Hz, 1H), 7.29-7.27 (m, 2H), 7.24 (s, 1H), 6.91 (d, J=8.4 Hz, 1H), 6.66 (s, 1H), 6.02 (s, 1H), 4.28 (s, 2H), 2.81 (s, 6H), 2.44 (s, 3H), 1.38 (s, 3H), 1.34 (s, 3H).

Example 8

Preparation of 4,4-difluoro-3-[3-(N,N-dimethylaminomethyl)-4-hydroxyphenyl]-8-phenyl-4-bora-3a,4a-diaza-s-indacene According to the procedure in Example 1, starting from 4,4-Difluoro-3-(4-hydroxyphenyl)-8-phenyl-4-bora-3a,4a-diaza-s-indacene (Intermediate 26, 57 mg, 0.15 mmol), Eschenmoser salt (21 mg, 0.23 mmol) and $K_2CO_3$ (31 mg, 0.23 mmol) the title product is obtained after chromatography.

Example 9

Preparation of 4,4-Difluoro-3-chloro-5-[3-(N,N-dimethylaminomethyl)-4-hydroxyphenyl]-8-phenyl-4-bora-3a,4a-diaza-s-indacene According to the procedure in Example 1, starting from 4,4-Difluoro-3-(4-hydroxyphenyl)-5-chloro-8-phenyl-4-bora-3a,4a-diaza-s-indacene (Intermediate 29, 1 mmol), Eschenmoser salt (1 mmol) and $K_2CO_3$ (2 mmol) the title product is obtained after chromatography.

Example 10

Preparation of 4,4-difluoro-3,5-dichloro-8-[3-(N,N-dimethylaminomethyl)-4-hydroxyphenyl]-4-bora-3a,4a-diaza-s-indacene According to the procedure in Example 1, starting from 4,4-Difluoro-3,5-dichloro-8-(4-hydroxyphenyl)-4-bora-3a,4a-diaza-s-indacene (Intermediate 13, 200 mg, 0.57 mmol) Eschenmoser salt (69 mg, 0.74 mmol) and $K_2CO_3$ (102 mg, 0.74 mmol) the title product is obtained after chromatography using using $CH_2Cl_2$/EtOAc/$CH_3OH$ (73:20:7) as eluent.

Example 11

Preparation of 4,4-difluoro-3,5-bis[3-(N,N-dimethylaminomethyl)-4-hydroxyphenyl]-8-phenyl-4-bora-3a,4a-diaza-s-indacene According to the procedure in Example 1, starting from 4,4-Difluoro-3,5-bis(4-hydroxyphenyl)-8-phenyl-4-bora-3a,4a-diaza-s-indacene (Intermediate 30, 0.1 mmol), Eschenmoser salt (0.1 mmol) and $K_2CO_3$ (0.2 mmol) the title product is obtained after chromatography.

Example 12

Preparation of 4,4-difluoro-1,7-dimethyl-3,5-bis{2[3-(N,N-dimethylaminomethyl)-4-hydroxyphenyl]ethenyl}-8-phenyl-4-bora-3a,4a-diaza-s-indacene According to the procedure in Example 1, starting from 4,4-Difluoro-8-phenyl-1,7-dimethyl-3,5-bis[2-(4-hydroxyphenyl)ethenyl)]-4-bora-3a,4a-diaza-s-indacene (Intermediate 19, 0.1 mmol), Eschenmoser salt (0.1 mmol) and $K_2CO_3$ (0.2 mmol) the title product is obtained after chromatography.

Biological Assays

The potential for a compound of the present invention to have an advantageous profile for providing therapeutic benefit in the treatment of oncological diseases and/or to have utility in fluorescent labelling of biological material may be demonstrated, for example, using the following assays:

Antiproliferative Assay

The described assay was used to test the effects of test compounds on the proliferation of various human tumor cell lines, whereby cytostatic and cytotoxic effects on cells can be differentiated. The experiments were carried out on human cell lines, which were derived from 3 tumor types: MCF-7 (breast carcinoma), HCT 116 (colon carcinoma), H 460 (lung carcinoma).

Cell lines were cultured as monolayers and maintained in Dulbecco's modified Eagle medium (DMEM), supplemented with 10% fetal bovine serum (FBS), 2 mM L-glutamine, 100 U/ml penicillin and 100 μg/ml streptomycin in a humidified atmosphere with 5% $CO_2$ at 37° C.

The cell lines were inoculated onto a series of standard 96-well microtiter plates on day 0, at $1\times10^4$ to $3\times10^4$ cells/ml, depending on the doubling times of the specific cell line. Test compounds were added next day to the cell lines in five consecutive 10-fold dilutions ($10^{-8}$ to $10^{-4}$ M) and incubated for a further 72 hours. Working dilutions were freshly prepared on the day of testing. The solvent (DMSO) was also tested for eventual inhibitory activity by adjusting its concentration to be the same as in working concentrations.

For each cell line one of the plates was left in the dark, while the other was irradiated in a Luzchem reactor (6 lamps 350 nm, 5 min; or 6 lamps 420 nm, 15 min, visible light, 15 min) four hours after the addition of the test compounds and subsequently 24 h and 48 h after the first irradiation, as described above. After 72 hours of incubation the cell growth rate was evaluated by performing the MTT assay (Mossman, Methods Immunol, 1983, 65, 55-63), which detects dehydrogenase activity in viable cells. The MTT Cell Proliferation Assay is a colorimetric assay system, which measures the reduction of a tetrazolium component (MTT) into an insoluble formazan produced by mitochondria of viable cells. For this purpose the substance treated medium was discarded and MTT was added to each well in concentration of 20 μg/40 μl. After four hours of incubation the precipitates were dissolved in 160 μl of dimethylsulphoxide (DMSO). The absorbance (OD, optical density) was measured on a microplate reader at 570 nm. The absorbance is directly proportional to the cell viability. The percentage of growth (PG) of the cell lines was calculated according to one of the following two equations (according to the National Cancer Institute protocols, www.dtp.nci.nih.gov):

If (mean $OD_{test}$-mean $OD_{tzero}$)≥0 then
PG=100×(mean $OD_{test}$-mean $OD_{tzero}$)/(mean $OD_{ctrl}$-mean$OD_{tzero}$).

If (mean $OD_{test}$-mean $OD_{tzero}$)<0 then:
PG=100×(mean $OD_{test}$-mean $OD_{tzero}$)/$OD_{tzero}$.

where:

Mean $OD_{tzero}$=the average of optical density measurements before exposure of cells to the test compound.

Mean $OD_{test}$=the average of optical density measurements after the desired period of time.

Mean $OD_{ctrl}$=the average of optical density measurements after the desired period of time with no exposure of cells to the test compound.

Each test point was performed in quadruplicate in three individual experiments. The results were expressed as $IC_{50}$, a concentration necessary for 50% of proliferation inhibition. Each result is a mean value from three separate experiments. The $IC_{50}$ measures the growth inhibitory power of the test agent and represents the concentration that causes 50% growth inhibition. The $IC_{50}$ is calculated from dose-response curves using linear regression analysis by fitting the test concentrations that give PG values above and below the respective reference value (e.g. 50% of inhibition for $IC_{50}$). Therefore, a "real" value for any of the response parameters is obtained only if at least one of the tested drug concentrations falls above, and likewise at least one falls below the respective reference value. If however, for a given cell line or test agent all of the tested concentrations produce PGs exceeding the respective reference level of effect (e.g. PG value of 50%), then the highest tested concentration is assigned as the default value. In the screening data report the default value is preceded by a ">" sign.

TABLE 3

Inhibition of HCT116, MCF-7 and H 460 cell lines ($IC_{50}$/μM [a]) by compounds in example 2, 4 and 7

| | Cell lines | | | | | | | | | | | |
|---|---|---|---|---|---|---|---|---|---|---|---|---|
| | HCT116 | | | | MCF-7 | | | | H 460 | | | |
| Comp. | Not irrad. | 350 nm 3 × 5 min | 420 nm 3 × 15 min | VIS 3 × 15 min | Not irrad. | 350 nm 3 × 5 min | 420 nm 3 × 15 min | VIS 3 × 15 min | Not irrad. | 350 nm 3 × 5 min | 420 nm 3 × 15 min | VIS 3 × 15 min |
| Examp. 2 | >100 | >100 | 37 ± 7 | 89 ± 6 | ≥100 | ≥100 | 25 ± 6 | 32 ± 25 | >100 | >100 | 30 ± 18 | 43 ± 6 |
| Examp. 4 | 16 ± 1 | 11 ± 2 | 2 ± 0.4 | 2 ± 0.1 | 13 ± 0.1 | 10 ± 0.6 | 2 ± 0.2 | 1.6 ± 0.01 | 13 ± 0.2 | 5 ± 3 | 1 ± 0.1 | 0.9 ± 0.2 |
| Examp. 7 | 27 | | | 2 | 22 ± 12 | | | 2 ± 0.7 | 20 ± 5 | | | 2 ± 0.7 |

[a] $IC_{50}$; the concentration that causes 50% growth inhibition

A compound analyzed using biological assays defined herein is considered to be active if it exhibits one of the following results:
a) the $IC_{50}$ values (in μM) after the irradiation is lower than $IC_{50}$ values for non-irradiated cells; and/or
b) the $IC_{50}$ values (in μM) for irradiated and/or non-irradiated cells is less than 100

Fluorescent Labeling of Proteins
Preparation of Total Cell Lysates

For protein staining analysis human mammary epithelial cell total lysates were used. The cells from a 80% confluent T75 cell culture flask were twice washed with phosphate buffer saline (PBS, 137 mM NaCl (Sigma, St Louis, Mo., USA), 2.7 mM KCl (Sigma, St Louis, Mo., USA), 4.3 mM Na₂HPO₄ (Sigma, St Louis, Mo., USA), 1.47 mM KH2 PO₄ (Sigma, St Louis, Mo., USA), pH 7.4) and subsequently lysed in 1 mL of lysis buffer containing 50 mM Tris pH 7.6 (Sigma, St Louis, Mo., USA), 150 mM NaCl (Sigma, St Louis, Mo., USA), 2 mM EDTA (Sigma, St Louis, Mo., USA), 1% NP-40 (BioRad, Hercules, Calif., USA) and supplemented with Complete Mini protease inhibitors (Roche Applied Science, Penzberg, Germany). The cells were shortly sonicated to ensure complete lysis and the cellular debris was removed by centrifugation at 16,000× g for 20 min at 4° C. The lysates were then stored at −80° C. Total proteins were measured using microassay procedure for Pierce™ BCA Protein Assay Kit (Thermo Fischer Scientific, Rockford, Ill., USA). The protein concentration was measured in microtiter 96 well plates. For each experiment a standard curve was determined using the 2 mg/mL BSA (Thermo Fischer Scientific, Rockford, Ill., USA) diluted to 1.0, 0.5, 0.25 and 0.125 mg/mL. The standard and sample concentrations were assayed in triplicates according to the manufacturer protocol. The absorbance was measured at 570 nm on plate reader (Multiskan EX Microplate Photometer, Thermo Fisher Scientific, Waltham, Mass., US). The $OD_{570}$ was corrected for blank and the sample protein concentration was calculated by linear equation of the standard.

Labeling of Proteins Resolved on SDS-PAGE with BODIPY of Formula (I)

Various concentrations of bovine serum albumin (BSA) dissolved in PBS or total cell lysate were mixed with 4× loading buffer (4:1, 250 mM Tris HCl, pH 6.8, 40% (v/v) glycerol (Sigma, St Louis, Mo., USA), 5% (p/v) SDS (Sigma, St Louis, Mo., USA)) and subjected to SDS-polyacrylamide gel electrophoresis using Mini-PROTEAN Tetra cell system for vertical electrophoresis (BioRad, Hercules, Calif., USA). Thermo Scientific PageRuler Plus Prestained Protein Ladder (Thermo Fischer Scientific, Rockford, Ill., USA) was used as a molecular weight marker. The polyacrylamide gels with resolved proteins were then incubated in PBS containing 1.33 mM BODIPY of Formula (I) in dark or irradiated with 450 nm light for 15 min. The gels were then rinsed in buffer containing 25 mM Tris, 192 mM glycin and 20% methanol. The proteins were visualized using UV transilluminator (Uvitec BXT-20.M). Additionally the same concentrations of BSA or total cell lysate were resolved on SDS-PAGE and stained with 0.1% Coomassie blue stain (Sigma, St Louis, Mo., USA) in 10% acetic acid (Sigma, St Louis, Mo., USA) and 40% methanol (Sigma, St Louis, Mo., USA). The destain buffer consisted of 20% methanol and 10% acetic acid.

Labeling of Proteins with BODIPY of Formula (I) Prior to the SDS-PAGE

Biological material (10 µg of BSA or 50 µg of the total cell lysate) was mixed with 1.33, 0.133 or 0.0133 mM BODIPY of Formula (I) and incubated on ice for 24 h in dark or in visible light. After the incubation, the samples were mixed with 4× loading buffer described above and subjected to SDS-polyacrylamide gel electrophoresis using Mini-PROTEAN Tetra cell system for vertical electrophoresis Thermo Scientific PageRuler Plus Prestained Protein Ladder was used as a molecular weight marker (m). The resolved proteins were visualized on UV transilluminator and subsequently stained with 0.1% Coomassie blue stain in 10% acetic acid and 40% methanol The destain buffer consisted of 20% methanol and 10% acetic acid.

The invention claimed is:

1. A compound of Formula (I):

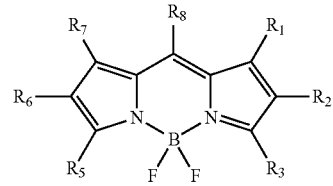

wherein
$R^1$, $R^2$, $R^6$ and $R^7$ are independently selected from H, Cl, Br and $C_1$-$C_4$ alkyl;
$R^3$ and $R^5$ are independently selected from H, Cl, Br, $C_1$-$C_4$ alkyl, aryl, —CH=CH-aryl, A and CH=CH-A;
$R^8$ is selected from aryl and A;
wherein aryl may be unsubstituted or substituted by 1-3 substituents selected from $C_1$-$C_4$ alkyl, $C_1$-$C_4$ haloalkyl, $C_1$-$C_4$ alkoxy and OH;
A is a substituent of formula:

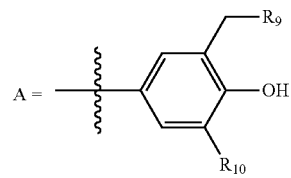

$R^9$ is selected from —N($C_1$-$C_4$ alkyl)₂, —N($C_1$-$C_4$ alkyl)₂H+X⁻ and —N($C_1$-$C_4$ alkyl)₃±X⁻,
X⁻ is Cl⁻ Br⁻, or I⁻;
$R^{10}$ is selected from H and —CH₂R⁹;
with the proviso that at least one of $R^3$, $R^5$ and $R^8$ is A or one of $R^3$ and $R^5$ is CH=CH-A;
or a salt thereof.

2. The compound or a salt thereof as claimed in claim 1, wherein $R^8$ is A.

3. The compound or a salt thereof as claimed in claim 1, wherein $R^3$ is A or —CH=CH-A.

4. The compound or a salt thereof as claimed in claim 1, wherein $R^3$ and $R^5$ are both A or —CH=CH-A.

5. The compound or a salt thereof as claimed in claim 1, wherein $R^3$ and $R^8$ are both A, or $R^3$ is —CH=CH-A and $R^8$ is A.

6. The compound or a salt thereof as claimed in claim 2, wherein $R^9$ is —N($C_1$-$C_4$ alkyl)₂H+X⁻ and $R^{10}$ is H.

7. The compound or a salt thereof as claimed in claim 6, wherein $R^9$ is —N(CH₃)₂H⁺X⁻.

8. The compound or a salt thereof as claimed in claim 2, wherein $R^1$, $R^2$, $R^6$ and $R^7$ are independently selected from H and $C_1$-$C_4$ alkyl.

9. The compound of Formula (I) or a salt thereof as claimed in claim 1, wherein the salt is a pharmaceutically acceptable salt.

10. The compound of Formula (I) as claimed in claim 1 or a pharmaceutically acceptable salt thereof for use in medical therapy.

11. The compound of Formula (I) as claimed in claim 1 or a pharmaceutically acceptable salt thereof for use in the treatment of cancer.

12. The compound of Formula (I) as claimed in claim 1, for use as a fluorescent labelling reagent.

13. A pharmaceutical composition comprising:
   a) a compound of Formula (I) as claimed in claim 1, or a pharmaceutically acceptable salt thereof and
   b) one or more pharmaceutically acceptable carriers.

\* \* \* \* \*